United States Patent [19]
Gubler et al.

[11] Patent Number: 5,840,530
[45] Date of Patent: Nov. 24, 1998

[54] DNA ENCODING RECEPTORS FOR THE BETA-2 CHAIN OF HUMAN IL-12

[75] Inventors: Ulrich Andreas Gubler; David Howard Presky, both of Glen Ridge, N.J.

[73] Assignee: Hoffmann-La Roche Inc., Nutley, N.J.

[21] Appl. No.: 685,118

[22] Filed: Jul. 23, 1996

[51] Int. Cl.$^6$ .............. C12N 15/09; C12N 15/03; C12N 15/11
[52] U.S. Cl. .......... 435/69.1; 435/361; 435/363; 435/252.3; 435/320.1; 536/23.5
[58] Field of Search .............. 536/23.5; 435/69.1, 435/361, 363, 252.3

[56] References Cited

U.S. PATENT DOCUMENTS 5,536,657  7/1996  Chua et al. .............. 435/69.1

OTHER PUBLICATIONS

Gately, M.K. et al., 1991, J. Immunol. 147:874.
Kobayashi, M., et al., 1989, J. Exp. Med. 170:827.
Stern, A.S. et al., 1990, Proc. Natl. Acad. Sci. USA 87:6808.
Gately, M.K., 1992, Cell Immunology 143:127.
Chan, S.H. et al., 1991, J. Exp. Med. 173:869.
Manetti, R., et al., 1993, J. Exp. Med. 177:1199.
Hsieh, C.S. et al., 1993, Science 260:547.
Chizzonite, R., et al., 1992, J. Immunol. 148:3117.
Desai, B., et al., J. Immunol, 1992, 148:3125.
Desai, B., et al., 1993, J. Immunol. 150:207A.
Chizzonite, R., et al., 1994, Cytokine 6(5):A82a.
Chua, A., et al., 1994, J. Immunology 153:128.
Stahl & Yancopoulos, 1993, Cell 74:587.
Charnow, S.M., et al., Trends in Biotechnology vol. 14 52–60 (1996).
M.O. Dayhoff, et al., Methods Enzymology 91:524 (1983).
U. Gubler, et al., 1991, Proc. Natl. Acad. Sci USA 88:4143.
H.W. Lahm et al., 1985, J. Chromatog. 326:357.
S. Mizushima & S. Nagata, Nucl. Acids. Res. 1990 18:5322.
S. Grant. et al. 1990, Proc. Natl. Acad. Sci. USA 87:4645.
Gately, et al., J. Natl. Cancer Inst. 69 1245 (1982).
P. Chomczynski & N. Sacchi, Anal. Biochem. 162: 156, 1987.
K. Kuribayashi et al. Nucl. Acids Res. Symposium Series 19:61, 1988.
U. Gubler & A. Chua, Essential Molecular Biology vol. II, T.A. Brown, editor pp. 39–56 TRL Press 1991.
A. Aruffo & B. Seed, Proc. Natl. Acad. Sci (USA) 94, 8573, 1987.
Hara & Miyajima 1992, EMBO 11:1875.
Grunstein & Hogness, Molecular Cloning Proc. Nat. Acad. Sci. USA 72:3961 (1975).
McPherson J., 1985, Pharmacol Methods, 14:213.
Palacios R., et al., 1985, Cell 41:727.
Giordano, T. J. et al., 1990, Gene 88:285.
vonHeijne G., 1986, Nucl. Acids Research 14:4683.
Presky, D., et al., Res. Immunol. 146 439–445 (1995).
Ellison et al., Nucl. Acid Res. 10 4071–4079.
Huck, et al., Nucl. Acid Res 14 1779–1789 (1986).
Presky, et al., PNAS 93(24), 14002–14007 (1996).
Gubler, et al., FASEB J. 10(6), A1326 (1996).
Szabo et al., FASEB J. 10(6), A1310 (1996).
Chizzonite et al *Cytokine* 6(5) 1994, A82a.
Chua et al *J Immunol* 153, 1994, p. 128.
Presky et al, Res Immunol 146, 1995, pp. 439–445.

*Primary Examiner*—Garnette D. Draper
*Attorney, Agent, or Firm*—George W. Johnston; Patricia S. Rocha-Tramaloni; Robert A. Silverman

[57] ABSTRACT

A recombinant human IL-12 beta2 receptor protein produced on the surface of a non-human mammalian cell, free from other human proteins, in its active form. In addition, a non-human mammalian cell having expressed on its surface the recombinant human IL-12 beta2 receptor protein, which cell proliferates in the presence of human IL-12. A non-human mammalian cell having the human IL-12 beta2 receptor protein on its surface and which proliferates in response to human IL-12 is useful for determining whether a given compound inhibits biological activity of human IL-12 or is an IL-12 agonist.

12 Claims, No Drawings

DNA ENCODING RECEPTORS FOR THE BETA-2 CHAIN OF HUMAN IL-12

FIELD OF INVENTION

This application claims the benefit of U.S. Provisional Application Nos: 60/001,701, filed 1 Aug. 1995 and 60/018,674, filed 30 May 1996.

This invention relates generally to human Interleukin-12 receptors.

BACKGROUND OF THE INVENTION

Interleukin-12 (IL-12), formerly known as cytotoxic lymphocyte maturation factor or natural killer cell stimulatory factor, is a 75-KDa heterodimeric cytokine composed of disulfide-bonded 40-KDa (p40) and 35-KDa (p35) subunits that has multiple biological activities including stimulation of the proliferation of activated T and NK cells (Gately, M. K., et al., 1991, J. Immunol., 147:874) (Kobayashi, M., et al., 1989, J. Exp. Med., 170:827), enhancement of the lytic activity of NK/LAK cells (Kobayashi, M., et al., 1989, J. Exp. Med., 170:827; Stern, A. S., et al., 1990, Proc. Natl. Acad. Sci. USA, 87:6808), enhancement of cytolytic T-cell responses (Gately, M. K., et al., 1992, Cell. Immunology, 143:127), induction of interferon gamma by resting and activated T- and NK-cells (Kobayashi, M. et al., 1989, J. Exp. Med., 170:827; Chan, S. H., et al., 1991, J. Exp. Med., 173:869), and promotion of $T_h1$-type helper cell responses (Manetti, R., et al., 1993, J. Exp. Med., 177:1199; Hsieh, C.-S., et al., 1993, Science 260:547).

The biological activity of IL-12 is mediated by the binding of the IL-12 molecules to cell surface, or plasma membrane, receptors on activated T- and NK cells; however, the contributions of the individual subunits, p35 and p40, to receptor binding and signal transduction remain unknown. Studies with labeled IL-12 have shown that this binding occurs in a specific and saturable manner. IL-12 delivers a signal to target cells through a receptor that was initially characterized on phytohaemagglutinin (PHA)-activated CD4+ and CD8+ T-cells and on IL-2 activated CD56+ NK-cells (Chizzonite, R., et al., 1992, J. Immunol., 148:3117; Desai, B., et al., 1992, J. Immunol., 148:3125).

A survey of over 20 human cell lines belonging to the T-, B-, NK- and myelomonocytic lineages only identified a single CD4+, IL-2 dependent human T-cell line (Kit 225/K6) that constitutively expresses the IL-12 receptor and responds to IL-12 (Desai, B., et al., 1992, J. Immunol., 148:3125; Desai, B., et al., 1993, J. Immunol. 150:207A). Freshly prepared PHA-activated peripheral blood mononuclear cells (PBMC) and the Kit 225/K6 cell line thus represent two convenient cell sources to study the biochemistry of the functional IL-12 receptor; there may be others.

Equilibrium binding experiments with $^{125}$I-labeled IL-12 identified three sites with binding affinities for human IL-12 of 5–20 pM, 50–200 pM, and 2–6 nM on IL-12 responsive T-cells (Chizzonite, R., et al., 1994, Cytokine 6(5):A82a).

A cDNA encoding a low affinity IL-12 receptor was previously cloned (Chua, A., et al, 1994, J. Immunology 153:128; U.S. patent application Ser. No. 08/248,532, filed May 31, 1994 now U.S. Pat. No. 5,536,657 (incorporated herein by reference)). Based on a previously suggested nomenclature (Stahl and Yancopoulos, 1993, Cell 74:587), we now call the initially isolated human IL-12 receptor chain the beta1 chain. However, because (i) this isolated human IL-12 beta1 receptor chain binds human IL-12 with low affinity, and (ii) IL-12 responsive T-cells have a high affinity binding site for human IL-12, another human IL-12 receptor chain must exist.

SUMMARY OF THE INVENTION

We have found that the IL-12 receptor comprises a complex of the beta1 receptor protein with a beta2 receptor protein, which complex is capable of binding to human IL-12 with high affinity. We have isolated the DNA encoding the human IL-12 beta2 receptor protein and produced a recombinant human IL-12 beta2 receptor protein on the surface of a non-human mammalian cell, free from other human proteins, in its active form. In addition, we produced a recombinant human IL-12 receptor complex on the surface of a non-human mammalian cell, free from other human proteins, having a high binding affinity for human IL-12. In addition, we produced a non-human mammalian cell having expressed on its surface the recombinant human IL-12 beta2 receptor protein, which cell proliferates in the presence of human IL-12. In addition, we produced a non-human mammalian cell having expressed on its surface the recombinant human IL-12 receptor complex, which cell proliferates in the presence of human IL-12.

In accordance with this invention, a non-human mammalian cell having the human IL-12 beta2 receptor protein or the complex expressed on its surface and which proliferates in response to human IL-12 is useful for determining IL-12 bioactivity. For example, such cells are useful for determining whether a given compound inhibits biological activity of human IL-12 or is an IL-12 agonist.

In addition, through the ability to express the human IL-12 beta2 receptor protein on a non-human mammalian cell surface, we can also express fragments of the human IL-12 beta2 receptor protein, and can determine whether these fragments, when complexed with the beta1 subunit, or an active fragment thereof, have the same properties and high binding affinity for IL-12 as the intact complex.

We can use the isolated DNA encoding the human IL-12 beta2 receptor protein to make a purified, recombinant protein which is soluble, and which binds to IL-12 with the same affinity as human IL-12 beta2 receptor protein. We can also use the isolated DNA encoding the human IL-12 beta2 receptor protein to make a purified, recombinant protein which is soluble, and which binds to IL-12 with the same affinity as the recombinant human IL-12 receptor complex of the beta1 receptor protein with the beta2 receptor protein [See, for example, Charnow, S. M. et al., Trends in Biotechnology, Vol. 14, 52–60 (1996)].

Such purified, recombinant proteins, which bind to human IL-12, are useful for preventing or treating pathological conditions caused by excess or inappropriate activity of cells possessing IL-12 receptors, by inhibiting binding of IL-12 to such cells. Pathological conditions caused by excess activity of cells possessing IL-12 receptors include autoimmune dysfunctions, such as without limitation rheumatoid arthritis, inflammatory bowel disease, and multiple sclerosis.

A purified, recombinant protein which is soluble, and which binds to IL-12 with the same affinity as human IL-12 beta2 receptor protein is the fusion of a soluble fragment of human IL-12 beta2 receptor protein and a human Ig heavy chain (such as IgG, IgM or IgE, preferably IgG) having all domains except the first domain of the constant region. This recombinant protein is encoded by a chimeric polynucleotide which has 2 DNA subsequences fused in frame. The first DNA subsequence, at the 5' end of the chimeric polynucleotide, is an isolated DNA sequence encoding a soluble fragment of human IL-12 beta2 receptor protein. The second DNA subsequence, located at the 3' end of the chimeric polynucleotide, is an isolated DNA sequence encoding all domains of a human heavy chain Ig (preferably IgG) except the first domain of the constant region. The desired recombinant protein can be generated by transfection of the chimeric polynucleotide into a non-human mammalian cell, such as a chinese hamster ovary (CHO) cell. The expressed recombinant protein can be purified, for example, by protein G affinity chromatography.

A purified, recombinant protein which is soluble, and which binds to IL-12 with the same affinity as the recombinant human IL-12 receptor complex of the beta1 receptor with the beta2 receptor is encoded by two chimeric polynucleotides which each have two DNA subsequences fused in frame. The first DNA subsequence of the first chimeric polynucleotide, located at the 5' end, is an isolated DNA sequence encoding a soluble fragment of human IL-12 beta2 receptor protein. The second DNA subsequence of the first chimeric polynucleotide, located at the 3' end, is an isolated DNA sequence encoding all domains of a human Ig heavy chain (for example, IgG, IgM, IgE, preferably IgG) except the first domain of the constant region. The first DNA subsequence of the second chimeric polynucleotide, located at the 5' end, is an isolated DNA sequence encoding a soluble fragment of human IL-12 beta1 receptor protein. The second DNA subsequence of the second chimeric polynucleotide, located at the 3' end, is an isolated DNA sequence encoding all domains of a human Ig heavy chain (for example, IgG, IgM, IgE, preferably IgG) except the first domain of the constant region. The desired recombinant protein may be generated by cotransfection of the two chimeric polynucleotides into a non human mammalian cell, such as a CHO cell. The expressed protein can be purified, for example, by any method that enables differentiation of homodimeric proteins from heterodimeric proteins, such as, for example, column chromatography.

In addition, monoclonal or polyclonal antibodies directed against the human IL-12 beta2 receptor protein, or fragments thereof, or the complex, may also be produced by known methods [See, for example, Current Protocols in Immunology, edt. by Coligan, J. E. et al., J. Wiley & Sons (1992)] and used to prevent or treat pathological conditions caused by excess activity of cells possessing IL-12 receptors by inhibiting binding of IL-12 to such cells.

DETAILED DESCRIPTION OF THE INVENTION

We have found that the human IL-12 receptor comprises a complex of the beta1 receptor protein with the beta2 receptor protein, which complex is capable of binding to human IL-12 with high affinity. We have isolated the DNA encoding the human IL-12 beta2 receptor protein and produced a recombinant human IL-12 beta2 receptor protein on the surface of a non-human mammalian cell, free from other human proteins, in its active form. In addition, we produced a recombinant human IL-12 receptor complex on the surface of a non-human mammalian cell, free from other human proteins, having a high binding affinity for human IL-12. In addition, we produced a non-human mammalian cell having expressed on its surface the recombinant human IL-12 beta2 receptor protein, which cell proliferates in the presence of human IL-12. In addition, we produced a non-human mammalian cell having expressed on its surface the recombinant human IL-12 receptor complex, which cell proliferates in the presence of human IL-12.

The following terms shall have the following definitions set forth below:

Human IL-12 beta2 receptor protein refers to (1) the protein of SEQ ID NO:2, or (2) any protein or polypeptide having an amino acid sequence which is substantially homologous to the amino acid sequence SEQ ID NO:2 and which has the following properties:

1) The protein or polypeptide has low binding affinity for human IL-12, and

2) The protein or polypeptide, when complexed with human beta1 receptor protein forms a complex having high binding affinity for human IL-12.

Human IL-12 beta1 receptor protein refers to (1) the protein of SEQ ID NO:4, or (2) any protein or polypeptide having an amino acid sequence which is substantially homologous to the amino acid sequence SEQ ID NO:4 and which has the following properties:

1) The protein or polypeptide binds to has low binding affinity for human IL-12, and 2) The protein or polypeptide, when complexed with human beta2 receptor protein forms a complex having high binding affinity for human IL-12.

As used herein, the terms human IL-12 beta2 receptor protein and human IL-12 beta1 receptor protein includes proteins modified deliberately, as for example, by site directed mutagenesis or accidentally through mutations.

Substantially homologous, which can refer both to nucleic acid and amino acid sequences, means that a particular subject sequence, for example, a mutant sequence, varies from the reference sequence by one or more substitutions, deletions, or additions, the net effect of which do not result in an adverse functional dissimilarity between the reference and subject sequences. For purposes of the present invention, sequences having greater than 95% homology, equivalent biological properties, and equivalent expression characteristics are considered substantially homologous. For purposes of determining homology, truncation of the mature sequence should be disregarded. Sequences having lesser degrees of homology, comparable bioactivity, and equivalent expression characterisitics are considered substantial equivalents. Generally, homologous DNA sequences can be identified by cross-hybridization under high stringency hybridization conditions.

Fragment of the human IL-12 beta2 receptor protein means any protein or polypeptide having the amino acid sequence of a portion or fragment of human IL-12 beta2 receptor protein, and which (a) has low binding affinity for human IL-12, and (2) when complexed with a human IL-12 beta1 receptor protein, forms a complex having high binding affinity for human IL-12.

Fragment of the human IL-12 beta1 receptor protein means any protein or polypeptide having the amino acid sequence of a portion or fragment of human IL-12 beta1 receptor protein, and which when complexed with a human IL-12 beta2 receptor protein, forms a complex having high binding affinity for human IL-12.

Expression vector is a genetic element capable of replication under its own control, such as a plasmid, phage or cosmid, to which another DNA segment may be attached so as to bring about the replication of the attached segment. It comprises a transcriptional unit comprising an assembly of (1) a genetic element or elements having a regulatory role in gene expression, for example, promoters and enhancers, (2) a structural or coding sequence which is transcribed into mRNA and translated into protein, and (3) appropriate transcription initiation and termination sequences.

Clone is a group of identical DNA molecules derived from one original length of DNA sequence and produced by a bacterium or virus using genetic engineering techniques, often involving plasmids.

Soluble fragment refers to a fragment of a human IL-12 receptor protein having an amino acid sequence corresponding to all or part of the extracellular region of the protein and which retains the IL-12 binding activity of the intact IL-12 receptor protein. For example, a soluble fragment of a human IL-12 beta2 receptor protein is a fragment of a human IL-12 beta2 receptor protein having an amino acid sequence corresponding to all or part of the extracellular region of a human IL-12 beta2 receptor protein.

Expression of Human IL-12 Receptor Protein
Having High Binding Affinity to Human IL-12

The cDNA of cells where the human IL-12 receptor is known to be found is incorporated by conventional methods into a bacterial host to establish a cDNA library. PHA-activated PBMC and cells from the Kit 225/K6 cell line are examples of cell sources for the cDNA. RNA from the cells is extracted, characterized, and transcribed into single stranded cDNA by conventional methods. The single stranded cDNA is converted into double stranded cDNA by conventional methods. The double stranded cDNA is incorporated by conventional techniques into an expression vector, such as pEF-BOS. The plasmid DNA from the expression vector is then incorporated into a bacterial host by conventional methods to form a library of recombinants.

The cDNA library is screened by conventional expression screening methods, as described by Hara and Mijayima, 1992, EMBO, 11:1875, for cDNA's which when expressed with cDNA's for the human IL-12 beta1 receptor protein, give rise to a high affinity human IL-12 receptor. A small number of clones from the library are grown in pools. DNA is extracted by conventional methods from the pools of clones. The DNA extracted from a pool of clones is then transfected by conventional methods, along with a small amount of DNA from a plasmid containing the cDNA encoding the human IL-12 beta1 receptor protein, into non-human host cells. The non-human host cells are preferably mammalian, such as a COS cell. Labeled recombinant human IL-12 is then added to the non-human host cells previously transfected as described above and the binding signal of the pool is determined. This process is repeated for each pool. The pools showing a positive binding signal for IL-12 may then be subsequently broken down into smaller pools and reassayed in the above manner until a single clone is selected which shows a positive binding signal.

The plasmid DNA from the selected clone is sequenced on both strands using conventional methods, such as an ABI automated DNA sequencer in conjunction with a thermostable DNA polymerase and dye-labeled dideoxynucleotides as terminators. Amino acid sequence alignments may be run as described by M. O. Dayhoff et al., Methods Enzymology 91:524 (1983) with the mutation data matrix, a break penalty of 6 and 100 random runs.

The DNA from the selected clone is then co-transfected by conventional methods with DNA from a plasmid containing the cDNA encoding the human IL-12 beta1 receptor protein into a non-human host cell, preferably a non-human mammalian cell such as a COS cell or a Ba/F3 cell.

Alternatively, by conventional recombinant methods, a plasmid may be engineered which contains transcription units (promoter, cDNA, and polyA regions) for both human IL-12 beta1 receptor protein and human IL-12 beta2 receptor protein. Plasmid DNA is transfected by conventional methods into a non-human host cell, preferably a non-human mammalian cell such as a COS cell or a Ba/F3 cell.

In accordance with the invention, a complex comprising human IL-12 beta2 receptor protein, or a fragment thereof, complexed with human IL-12 beta1 receptor protein, or a fragment thereof, may be expressed on the cell surface of the non-human host cell. When expressed on the cell surface of the non-human host cell, the complex has a high binding affinity for human IL-12, whereas the human IL-12 beta1 receptor protein and the human IL-12 beta2 receptor protein alone each have a low binding affinity for human IL-12.

In accordance with this invention, we can also express on the surface of a non-human host cell human IL-12 beta2 receptor protein.

In accordance with this invention, not only can the human IL-12 beta2 receptor protein be obtained, we can also obtain fragments of human IL-12 beta2 receptor protein which (1) has low binding affinity for human IL-12 and (2) which when complexed with a human IL-12 beta1 receptor protein forms a complex having high binding affinity. The fragments of human IL-12 beta2 receptor protein may be obtained by conventional means, such as (i) proteolytic degradation of the human IL-12 beta2 receptor protein, (ii) chemical synthesis by methods routine in the art, or (iii) standard recombinant methods.

For purposes of the present invention, a human IL-12 receptor protein which has a high binding affinity for human IL-12 is a protein which binds to human IL-12 with a binding affinity of from about 5 to about 100 pM. For purposes of the present invention, a human IL-12 receptor protein which has a low binding affinity for human IL-12 is a protein which binds to human IL-12 with a binding affinity of from about 1 to about 10 nM. The binding affinity of a protein for human IL-12 can be determined by conventional means, such as desribed in R. Chizzonite et al., 1992, J. Immunol., 148:3117 and as set forth in Example 5.

Fragments of human IL-12 beta2 receptor protein can also be measured for binding affinity for human IL-12 by conventional means, such as desribed in R. Chizzonite et al., 1992, J. Immunol., 148:3117 and as set forth in Example 5. The fragments of human IL-12 beta2 receptor protein may be measured for binding affinity for human IL-12 either alone or complexed with human IL-12 beta1 receptor protein, or a fragment of human IL-12 beta1 receptor protein which when complexed with a human IL-12 beta2 receptor protein forms a complex having high binding affinity.

In accordance with this invention, we can isolate DNA which encodes a complex capable of binding to human IL-12 with high affinity, the complex comprising human IL-12 beta2 receptor protein, or a fragment thereof, and human IL-12 beta1 receptor protein, or a fragment thereof.

In accordance with this invention, we can also isolate DNA which encodes human IL-12 beta2 receptor protein, or a fragment thereof, which fragment (1) has low binding affinity for human IL-12 and (2) when complexed with human IL-12 beta1 receptor protein, forms a complex having high binding affinity for human IL-12.

An isolated DNA sequence refers to a DNA polymer, in the form of a separate fragment or as a component of a larger DNA construct, which has been derived from DNA isolated at least once in substantially pure form, that is, free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used as a source of coding sequences. Sequences of non-translated DNA may be present 5' or 3' from the open reading frame, where the same do not interfere with manipulation or expression of the coding regions.

In accordance with this invention, we can also make, by known methods, a purified, recombinant protein which is the fusion of a soluble fragment of human IL-12 beta2 receptor protein and a human Ig heavy chain (preferably IgG) containing all domains except the first domain of the constant region. This recombinant protein, which is homodimeric, is encoded by a chimeric polynucleotide which has 2 DNA subsequences fused in frame. The first DNA subsequence, at the 5' end of the chimeric polynucleotide, is an isolated DNA sequence encoding a soluble fragment of human IL-12 beta2 receptor protein. The second DNA subsequence, located at the 3' end of the chimeric polynucleotide, is an isolated DNA sequence encoding all domains of a human Ig heavy chain (preferably IgG) except the first domain of the constant region.

In addition, we can make, by known methods, a purified, recombinant protein comprising two different polypeptide chains (a heterodimeric protein). The two different polypeptide chains are each encoded by a different chimeric polynucleotide which has two DNA subsequences fused in frame. The first DNA subsequence of the first chimeric polynucleotide, located at its 5' end, is an isolated DNA sequence encoding a soluble fragment of human IL-12 beta2 receptor protein. The second DNA subsequence of the first chimeric polynucleotide, located at its 3' end, is an isolated DNA sequence encoding all domains of a human Ig heavy chain (preferably IgG) except the first domain of the constant region. The first DNA subsequence of the second chimeric polynucleotide, located at its 5' end, is an isolated DNA sequence encoding a soluble fragment of human IL-12 beta1 receptor protein. The second DNA subsequence of the second chimeric polynucleotide, located at its 3' end, is an isolated DNA sequence encoding all domains of a human Ig heavy chain (preferably IgG) except the first domain of the constant region.

The starting materials for the purified, recombinant proteins of the invention may be obtained by methods known in the art. In particular, on the basis of the DNA sequence coding for human IL-12 beta2 receptor protein described in SEQ ID NO:1 and of the already known DNA sequences for certain receptors, those partial DNA sequences which code for a soluble fragment of human IL-12 beta2 receptor protein can be determined and engineered from the DNA sequence coding for human IL-12 beta2 receptor protein described in SEQ ID NO:1 using known methods, see Sambrook et al., "Molecular Cloning", 2nd ed., Cold Spring Harbor Laboratory Press (1989). Similarly, on the basis of the DNA sequence coding for human IL-12 beta1 receptor protein described in SEQ ID NO:3 and of the already known DNA sequences for certain receptors, those partial DNA sequences which code for a soluble fragment of human IL-12 beta1 receptor protein can be determined and engineered from the DNA sequence coding for human IL-12 beta1 receptor protein described in SEQ ID NO:3 using known methods, see Sambrook et al., "Molecular Cloning", 2nd ed., Cold Spring Harbor Laboratory Press (1989). Sources for isolated DNA sequences coding for constant domains of human immunoglobulins are known in the art and disclosed, for example, by Ellison et al., Nucl. Acid Res. 10, 4071–4079 (1982) for $IgG_1$ or Huck et al., Nucl. Acid Res. 14, 1779–1789 (1986) for $IgG_3$.

The isolated DNA sequence encoding the soluble fragment of human IL-12 beta2 receptor protein may be fused in frame, by known methods [Sambrook et al., "Molecular Cloning", 2nd ed., Cold Spring Harbor Laboratory Press (1989)], to the isolated DNA sequence encoding all domains of a human Ig heavy chain (preferably IgG) except the first domain of the constant region. The resulting chimeric polynucleotide has located at its 5' end the isolated DNA sequence encoding the soluble fragment of human IL-12 beta2 receptor protein and at its 3' end the isolated DNA sequence encoding all domains of the human Ig heavy chain except the first domain of the constant region.

Similarly, the isolated DNA sequence encoding the soluble fragment of human IL-12 beta1 receptor protein may be fused in frame, by known methods [Sambrook et al., "Molecular Cloning", 2nd ed., Cold Spring Harbor Laboratory Press (1989)], to the isolated DNA sequence encoding all domains of a human Ig heavy chain (preferably IgG) except the first domain of the constant region. The resulting chimeric polynucleotide has located at its 5' end the isolated DNA sequence encoding the soluble fragment of human IL-12 beta1 receptor protein and at its 3' end the isolated DNA sequence encoding all domains of a human Ig heavy chain except the first domain of the constant region.

The chimeric polynucleotides can then be integrated using known methods [Sambrook et al., "Molecular Cloning", 2nd ed., Cold Spring Harbor Laboratory Press (1989)] into suitable expression vectors for expression in a non-human mammalian cell, such as a CHO cell. In order to make the homodimeric protein of the invention, the chimeric polynucleotide having located at its 5' end the isolated DNA sequence encoding the soluble fragment of human IL-12 beta2 receptor protein is integrated into a suitable expression vector. In order to make the heterodimeric protein of the invention, the chimeric polynucleotide having located at its 5' end the isolated DNA sequence encoding the soluble fragment of human IL-12 beta2 receptor protein and the chimeric polynucleotide having located at its 5' end the isolated DNA sequence encoding the soluble fragment of human IL-12 beta1 receptor protein are integrated into a single suitable expression vector, or two separate suitable expression vectors.

Preferably, the chimeric polynucleotide(s) is/are co-transfected together with a selectable marker, for example neomycin, hygromycin, dihydrofolate reductase (dhfr) or hypoxanthin guanine phosphoribosyl transferase (hgpt) using methods which are known in the art. The DNA sequence stably incorporated in the chromosome can subsequently be amplified. A suitable selection marker for this is, for example, dhfr. Mammalian cells, for example, CHO cells, which contain no intact dhfr gene, are thereby incubated with increasing amounts of methotrexate after transfection has been performed. In this manner, cell lines which contain a higher number of the desired DNA sequence than the unamplified cells can be obtained.

The baculovirus expression system can also be used for the expression of recombinant proteins in insect cells. Post-translational modifications performed by insect cells are very similar to those occurring in mammalian cells. For the production of a recombinant baculovirus which expresses the desired protein a transfer vector is used. A transfer vector is a plasmid which contains the chimeric polynucleotide(s) under the control of a strong promoter, for example, that of the polyhedron gene, surrounded on both sides by viral sequences. The transfer vector is then transfected into the insect cells together with the DNA sequence of the wild type baculovirus. The recombinant viruses which result in the cells by homologous recombination can then be identified and isolated according to known methods. When using the baculovirus expression system, DNA sequences encoding the immunoglobulin part have to be in the form of cDNA.

The expressed recombinant protein may be purified, for example, by known methods. For example, protein G affinity chromatography may be used to purify the homodimeric protein of the invention. Column chromatography, or any other method that enables differentiation between homodimeric proteins and heterodimeric proteins, may be used to purify the heterodimeric protein of the invention.

Such purified, recombinant proteins are useful for preventing or treating pathological conditions caused by excess or inappropriate activity of cells possessing IL-12 receptors by inhibiting binding of IL-12 to such cells.

"Purified", as used to define the purity of a recombinant protein encoded by the combined DNA sequences described above, or protein compositions thereof, means that the protein or protein composition is substantially free of other proteins of natural or endogenous origin and contains less than about 1% by mass of protein contaminants residual of production processes. Such compositions, however, can contain other proteins added as stabilizers, carders, excipients or co-therapeutics. A protein is purified if it is detectable, for example, as a single protein band in a polyacrylamide gel by silver staining.

Purified recombinant proteins as described above (as well as antibodies to the human IL-12 beta2 receptor proteins and fragments thereof, and antibodies to the complex of this invention) can be administered in clinical treatment of autoimmune dysfunctions, such as without limitation rheumatoid arthritis, inflammatory bowel disease and multiple sclerosis.

The purified recombinant proteins described above (as well as antibodies to the human IL-12 beta2 receptor proteins and fragments thereof, and antibodies to the complex of this invention) can be used in combination with other cytokine antagonists such as antibodies to the IL-2 receptor, soluble TNF (tumor necrosis factor) receptor, the IL-1 antagonist, and the like to treat or prevent the above disorders or conditions.

The dose ranges for the administration of the purified, recombinant proteins described above (as well as antibodies to the human IL-12 beta2 receptor proteins and fragments thereof, and antibodies to the complex of this invention) may be determined by those of ordinary skill in the art without undue experimentation. In general, appropriate dosages are those which are large enough to produce the desired effect, for example, blocking the binding of endogenous IL-12 to its natural receptor. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The purified, recombinant proteins described above (as well as antibodies to the human IL-12 beta2 receptor proteins and fragments thereof, and antibodies to the complex of this invention) can be administered parenterally by injection or by gradual perfusion over time. They can be administered intravenously, intraperitoneally, intramuscularly, or subcutaneously.

Preparations for parenteral adminstration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcohol/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replinishers, electrolyte replinishers, such as those based on Ringer's dextrose, and the like. Preservatives and other additives may also be present, such as, for example, anti-micorbials, anti-oxidants, chelating agents, inert gases and the like. See, generally, *Remington's Pharmaceutical Science,* 16th Ed., Mack Eds., 1980.

Assays for Determining Whether a Given Compound Blocks IL-12 Activity

An aspect of the invention is the use of either the human IL-12 beta2 receptor protein or the complex of this invention as a screening agent for pharmaceuticals. In accordance with this invention, we can determine whether a given compound blocks human IL-12 activity or acts as an agonist of IL-12.

A biological activity of human IL-12 is the stimulation of the proliferation of activated T- and NK-cells. Proliferation of activated T-cells causes alloantigen-induced immune responses, such as allograft rejection (such as skin, kidney, and heart transplants) and graft-versus-host reaction in patients who have received bone marrow transplants. This biological activity of human IL-12 is mediated by the binding of the human IL-12 molecules to cell surface receptors on the activated T-cells.

A compound that blocks human IL-12 activity would, therefore, inhibit the proliferation of activated T-cells and would be useful to treat or prevent alloantigen induced immune responses.

In order to determine if a compound blocks human IL-12 activity, first, a plurality of cells having expressed on their surface either the human IL-12 beta2 receptor protein or a fragment thereof, or the complex of the invention, which cells proliferate in the presence of human IL-12, is provided. The human IL-12 beta2 receptor protein or a fragment thereof binds to human IL-12 with low binding affinity, but when complexed with human beta1 receptor protein forms a complex having high binding affinity for human IL-12. The complex of the invention binds to human IL-12 with high binding affinity and comprises a complex of (1) human IL-12 beta2 receptor protein, or a fragment thereof which when complexed with a human IL-12 beta1 receptor protein forms a complex having high binding affinity to human IL-12, and (2) human IL-12 beta1 receptor protein, or a fragment thereof which when complexed with a human IL-12 beta2 receptor protein forms a complex having high binding affinity to human IL-12. Second, the cells are contacted with human IL-12 and the given compound. Third, it is determined whether the presence of the given compound inhibits proliferation of the cells.

In order to determine if a compound is an agonist of human IL-12, first, a plurality of cells having expressed on their surface either the human IL-12 beta2 receptor protein or a fragment thereof, or the complex of the invention, and which cells proliferate in the presence of human IL-12, is provided. The human IL-12 beta2 receptor protein or a fragment thereof binds to human IL-12 with low binding affinity, but when complexed with human beta1 receptor protein forms a complex having high binding affinity for human IL-12. The complex of the invention binds to human IL-12 with high binding affinity and comprises a complex of (1) human IL-12 beta2 receptor protein, or a fragment thereof which when complexed with a human IL-12 beta1 receptor protein forms a complex having high binding affinity to human IL-12, and (2) human IL-12 beta1 receptor protein, or a fragment thereof which when complexed with a human IL-12 beta2 receptor protein forms a complex having high binding affinity to human IL-12. Second, the cells are contacted with human IL-12 or the given compound. Third, it is determined whether the presence of the given compound stimulates proliferation of the cells.

Examples of cells capable of expressing on their surface the complex, which cells proliferate in the presence of human IL-12 include, without limitation, PHA-activated PBMC, Kit 225/K6 cells, and Ba/F3 cells transfected with cDNA for both human IL-12 beta1 receptor protein and human IL-12 beta2 receptor protein. Examples of cells capable of expressing on their surface the human IL-12 beta2 receptor protein, or a fragment thereof, which cells proliferate in the presence of human IL-12 include, without limitation, Ba/F3 cells transfected with cDNA for human IL-12 beta2 receptor protein.

In order to determine whether the presence of the given compound inhibits proliferation of the cells, the following procedure may be carried out. The human IL-12 responsive cells, having expressed on their surface the human IL-12 beta2 receptor protein, or a fragment thereof, or the human IL-12 receptor complex of the invention, are plated into wells of a microtiter plate. Human IL-12 is then added to some wells of the microtiter plate (standard wells) and allowed to react with the cells. The compound to be tested is added either before or simultaneously with human IL-12 to different wells of the microtiter plate (sample wells) and allowed to react with the cells. Any solvent used must be non-toxic to the cell. The proliferation of the cells is then measured by known methods, for example, labeling the cells after contact with human IL-12 and the compound (such as by incorporation of tritiated thymidine into the replicating DNA), measuring the accumulation of cellular metabolites (such as lactic acid), and the like. The proliferation of the cells of the standard wells is compared to proliferation of the cells of the sample wells. If the cells of the sample wells proliferate significantly less than the cells of the standard wells, the compound blocks IL-12 activity.

In order to determine whether the presence of the given compound simulates proliferation of the cells, the following procedure may be carried out. The human IL-12 responsive cells having expressed on their surface the human IL-12 beta2 receptor protein, or a fragment thereof, or the human IL-12 receptor complex of the invention are plated into wells of a microtiter plate. Human IL-12 is then added to some wells of the microtiter plate (standard wells) and allowed to react with the cells. The compound to be tested is added to different wells of the microtiter plate (sample wells) and allowed to react with the cells. Any solvent used must be non-toxic to the cell. The proliferation of the cells is then measured by known methods, for example, labeling the cells after contact with the compound (such as by incorporation of tritiated thymidine into the replicating DNA), measuring the accumulation of cellular metabolites (such as lactic acid), and the like. The proliferation of the cells of the standard wells is compared to proliferation of the cells of the sample wells. If the cells of the sample wells proliferate significantly more than cells that were not exposed to human IL-12, the compound is an agonist of human IL-12.

The following examples are offered by way of illustration, not by limitation.

DETAILED DESCRIPTION OF THE PREFERRED EMBODIMENTS

Materials

Proteins, Plasmids and Strains

Recombinant human IL-12 (U. Gubler et al., 1991, Proc. Natl. Acad. Sci. USA., 88:4143) was obtained as described therein.

Recombinant human IL-2 (H. W. Lahm et al., 1985, J. Chromatog, 326:357) was obtained as described therein.

The plasmid pEF-BOS was obtained from Dr. Nagata at the Osaka Bioscience Institute in Japan. The plasmid is based on a pUC 119 backbone and contains the elongation factor 1 alpha promoter to drive expression of genes inserted at the BstXI site (S. Mizushima and S. Nagata, Nucl. Acids Res., 1990, 18:5322).

The human IL-12 receptor beta1 cDNA in the plasmid pEF-BOS was obtained as described in A. Chua et al., 1994, J. Immunology 153:128 and in U.S. patent application Ser. No. 08/248,532, filed May 31, 1994 now U.S. Pat. No. 5,536,657.

Electrocompetent $E.$ $coli$ DH-10B (S. Grant et al., 1990, Proc. Natl. Acad. Sci USA 87:4645) was obtained from Bethesda Research Laboratory (Bethesda, Md.).

Methods

Labeling of Human IL-12 with $^{125}I$

Recombinant human IL-12 was labeled with $^{125}I$ as follows. Iodogen was dissolved in chloroform. 0.05 mg aliquots of Iodogen were dried in 12×150 mm borosilicate glass tubes. For radiolabeling, 1.0 mCi Na[$^{125}I$] was added to the Iodogen-coated borosilicate glass tube, which also contained 0.05 ml of Tris-iodination buffer (25 mM Tris-HCL pH 7.5, 0.4M NaCl and 1 mM EDTA) to form a $^{125}I$ solution. The $^{125}I$ solution was activated by incubating for 6 minutes at room temperature. The activated $^{125}I$ solution was transferred to a tube containing 0.05 to 0.1 ml recombinant human IL-12 (31.5 $\mu$g) in Tris-iodination buffer. The resulting mixture of the activated $^{125}I$ solution and the recombinant human IL-12 was incubated for 6 minutes at room temperature. At the end of the incubation, 0.05 ml of Iodogen stop buffer (10 mg/ml tyrosine, 10% glycerol in Dulbecco's phosphate buffered saline (PBS), pH 7.40) was added and reacted for 3 minutes. The resulting mixture was then diluted with 1.0 ml Tris-iodination buffer containing 0.25% bovine serum albumin (BSA), and applied to a Bio-Gel P10DG desalting column for chromatography. The column was eluted with Tris-iodination buffer containing 0.25% BSA. 1 ml fractions containing the eluted peak amounts of labeled recombinant human IL-12 were combined. The combined fractions were diluted to $1\times10^8$ cpm/ml with 1% BSA in Tris-iodination buffer. Incorporation of $^{125}I$ into recombinant human IL-12 was monitered by precipitation with trichloroacetic acid (TCA). The TCA precipitable radioactivity (10% TCA final concentration) was typically in excess of 95% of the total radioactivity. The radiospecific activity of the labeled recombinant human IL-12 was typically 1000 to 2000 cpm/fmole.

EXAMPLE 1

Preparation of Human PHA-activated Lymphoblasts

Human peripheral blood mononuclear cells (PBMC) were isolated from blood collected from healthy donors as described in Gately et al., J. Natl. Cancer Inst. 69, 1245 (1982). The blood was collected into heparinized syringes, diluted with an equal volume of Hank's balanced salt solution and layered over lymphocyte separation medium (LSM® obtained from Organon Teknika Corporation, Durham, N.C.) in tubes. The tubes were spun at 2000 rpm for 20 minutes at room temperature. PBMC at the interface of the aqueous blood solution and the lymphocyte separation medium were collected. Collected PBMC were pelleted at 1500 rpm for 10 minutes through a 15 ml cushion of 20% sucrose in Hank's balanced salt solution. Pelleted PBMC were resuspended in tissue culture medium (1:1 mixture of RPMI 1640 and Dulbecco's modified Eagle's medium, supplemented with 0.1 mM nonessential amino acids, 60 µg/ml arginine HCl, 10 mM Hepes buffer, 2 µM L-glutamine, 100 U/ml penicillin, 100 µg/ml streptomycin, 0.05 mM 2-mercaptoethanol, and 1 µg/ml dextrose) (TCM) plus 5% human serum and washed twice in TCM.

The PBMC were then activated to form lymphoblasts. In particular, 0.5–1×10$^6$ cells/ml in TCM plus 5% human serum plus 0.1% (v/v) PHA-P (Difco, Detroit, Mich.) were cultured for 3 days at 37° C. in a 5% $CO_2$ atmosphere.

After three days, cell cultures were split 1:1 by volume in TCM plus 5% human serum and 50 U/ml recombinant human IL-2 to yield >95% T-cells. These cells were utilized for preparation of a cDNA library.

EXAMPLE 2

Extraction and Characterization of RNA

PBMC isolated as in Example 1, activated with PHA for 2–3 days, were harvested and total RNA was extracted using Guanidine Isothiocyanate/Phenol as described by P. Chomczynski and N. Sacchi, Anal. Biochem., 162:156, 1987. PolyA$^+$ RNA was isolated from the total RNA by one batch adsorption to oligo dT latex beads as described (K. Kuribayashi et al., Nucl. Acids Res. Symposium Series 19:61, 1988). The mass yield of this purification was about 4% of polyA+ RNA.

EXAMPLE 3 cDNA Library

From the above polyA$^+$ RNA, a cDNA library was established in the mammalian expression vector pEF-BOS as follows.

3 µg of polyA$^+$ RNA were reverse transcribed into single stranded cDNAs using RNaseH minus reverse transcriptase in the presence of α-$^{32}$P-dCTP. The resulting single stranded cDNAs were converted into blunt ended double stranded cDNAs as described by U. Gubler and A. Chua, Essential Molecular Biology Volume II, T. A. Brown, editor, pp. 39–56, IRL Press 1991. BstXI linkers (A. Aruffo and B. Seed, Proc. Natl. Acad. Sci (USA) 84, 8573, 1987) were ligated to the resulting double stranded cDNAs.

cDNA molecules having a size of greater than 800 base pairs (bp) were selected by size exclusion chromatography as follows. A Sephacryl SF 500 column (0.8×29 cm) was packed by gravity in 10 mM Tris-HCl pH 7.8—1 mM EDTA—100 mM NaAcetate. The radioactive cDNA with added BstXI linkers was applied to the column and 0.5 ml fractions were collected. The size distribution of radioactive cDNA was determined by performing electrophoresis on a small aliquot of each fraction on a 1% agarose gel, drying the gel, and visualizing the size by exposure of the gel to X-ray film. cDNA molecules larger than 800 bp were size selected in this fashion.

The selected cDNA molecules were pooled and concentrated by ethanol precipitation. The pooled and concentrated selected cDNA molecules were subsequently ligated to the plasmid pEF-BOS as follows. The plasmid had been restricted with BstXI and purified over two consecutive 1% agarose gels. 300 ng of the restricted and purified plasmid DNA were ligated to 30 ng of size selected cDNA in 60 µl of ligation buffer (50 mM Tris-HCl pH 7.8—10 mM $MgCl_2$—10 mM DTT—1 mM rATP—25 mg/ml BSA) at 15° C. overnight.

The following day, the plasmid ligated with the size selected cDNA was extracted with phenol. 6 mg of mussel glycogen were added to the resulting extract, and the nucleic acids were precipitated by ethanol. The resulting precipitate was dissolved in water and the nucleic acids again were precipitated by ethanol, followed by a wash with 80% ethanol. A pellet was formed from the precipitated and washed nucleic acids. The pellet was dissolved in 6 µl of water. 1 µl aliquots of the dissolved pellet were subsequently electroporated into E. coli strain DH-10B. Upon electroporation of 5 parallel aliquots, a library of about 10 million recombinants was generated.

EXAMPLE 4

Expression Screening for cDNAs Encoding High Affinity IL-12 Receptors

The library was screened according to the general expression screening method described by Hara and Miyajima, 1992, EMBO, 11:1875.

Pools of about 100 E. coli clones from the above library were grown and the plasmid DNA was extracted from the pools by conventional methods. 2×10$^5$ COS cells were plated per 35 mm culture well. COS cells were transfected with a transfection cocktail using the standard DEAE dextran technique described in "Molecular Cloning, a Laboratory Manual", 2nd Ed., J. Sambrook et al., Cold Spring Harbor Laboratory Press, 1989 ("Molecular Cloning"). The transfection cocktail contained (1) 1 µg of plasmid DNA extracted from the E. coli clone pools derived from the above library, and (2) 0.1 µg of pEF-BOS plasmid DNA containing the human IL-12 receptor beta1 cDNA.

3 days after transfection, the wells of COS cells were incubated with 10 pM labeled human recombinant IL-12 (specific activity=1000–2000 cpm/fmole) for 90 minutes at room temperature. The labeled human recombinant IL-12 was removed, and the COS cell monolayer was washed for one hour three times with binding buffer (RPMI 1640, 5% fetal bovine serum (FBS), 25 mM HEPES pH 7) to further select for COS cells expressing high affinity IL-12 receptors only (the binding of the IL-12 ligand to the low affinity sites was further reduced because the low affinity sites have a higher dissociation rate). Subsequently, the cell monolayers were lysed and counted in a gamma counter. After screening 440 pools (representing about 44,000 clones), one pool consistently showed a positive binding signal (300 cpm over 100 cpm background). From this pool, a single clone was subsequently isolated by sib-selection. This single clone (B5-10) contained a cDNA insert of about 3 kb that was completely sequenced.

The cDNA insert of clone B5-10 was incomplete with regard to the protein coding region because it did not contain an in-frame stop codon. The cDNA library of Example 3 was rescreened by conventional DNA hybridization techniques with the cDNA insert from clone B5-10, as described in Molecular Cloning and by Grunstein and Hogness, 1975, Proc. Nat. Acad. Sci. USA., 72:3961. Additional clones were thus isolated and then partially sequenced. The nucleotide sequence of one clone (No. 3) was found to (i) overlap with the 3' end of the nucleotide sequence of clone B5-10, (ii) extend beyond the nucleotide sequence of clone B5-10, and (iii) contain an in-frame stop codon.

This composite DNA sequence is shown in SEQ ID NO:1. The deduced amino acid sequence for the encoded receptor protein is shown in SEQ ID NO:2. Based on the previously suggested nomenclature of Stahl and Yancopolous, 1993, Cell 74:587, we call this newly isolated human IL-12 receptor chain the beta2 chain.

EXAMPLE 5

Binding Assays

COS cells (4–5×10$^7$) were transfected by electroporation using a BioRad Gene Pulser (250 μF, 250 volts) with either (1) 25 μg of the B5-10 plasmid DNA expressing recombinant human IL-12 beta2 receptor protein, (2) 25 μg of the pEF-BOS plasmid DNA expressing recombinant human IL-12 beta1 receptor protein, or (3) a mixture of 12.5 μg of the B 5-10 plasmid DNA expressing recombinant human IL-12 beta2 receptor protein and 12.5 μg of the pEF-BOS plasmid DNA expressing recombinant human IL-12 beta1 receptor protein. The electroporated cells were plated in a 600 cm$^2$ culture plate, harvested after 72 hours by scraping, washed and resuspended in binding buffer.

The cells were assayed to determine affinities of the expressed IL-12 receptors for human IL-12. In particular, equilibrium binding of labeled recombinant human IL-12 to the cells was performed and analyzed as described by R. Chizzonite, et al., 1992, J. Immunol., 148:3117. Electroporated cells (8×10$^4$) were incubated with increasing concentrations of $^{125}$I-labeled recombinant human IL-12 at room temperature for 2 hours. Incubations were carried out in duplicate or triplicate.

Cell bound radioactivity was separated from free labeled $^{125}$I-IL-12 by centrifugation of the mixture of electroporated cells and $^{125}$I-labeled recombinant human IL-12 through 0.1 ml of an oil mixture (1:2 mixture of Thomas Silicone Fluid 6428-R15 {A. H. Thomas} and Silicone Oil AR 200 {Gallard-Schlessinger}) at 4° C. for 90 seconds at 10,000×g to form a cell pellet in a tube. The cell pellet was excised from the tip of the tube in which it was formed, and cell bound radioactivity was determined in a gamma counter.

Receptor binding data were analyzed and the affinities were calculated according to Scatchard using the method described by McPherson, J., 1985, Pharmacol. Methods, 14:213.

EXAMPLE 6

Production of IL-12 Responsive Cell Line

Wild-type Ba/F3 cells, an IL-3-dependent mouse pro-B cell (Palacios, R. et al., 1985, Cell 41:727) and Ba/F3 cells expressing human IL-12 beta1 receptor protein (Chua, A., et al., 1994, J. Imunology 153:128) were cotransfected with (1) 80 μg of pEF-BOS plasmid DNA expressing recombinant human IL-12 beta2 receptor protein and (2) 8 μg of a plasmid expressing a hygromycin resistance gene (Giordano, T. J., et al., 1990, Gene 88:285) by electroporation using a BioRad Gene Pulser (960 μF, 400 volts).

All cells were resuspended at a density of 2×10$^5$ viable cells/ml in a growth medium of RPMI 1640, 10% FBS, glutamine (2 mM), penicillin G (100 U/ml), streptomycin (100 μg/ml), and 10% conditioned medium from the WEHI-3 cell line (ATCC No. TIB 68, American Type Culture Collection, Rockville, Md.). The WEHI-3 cell line is a source of IL-3. The resuspended cells were then incubated at 37° C. under 5% CO$_2$ for 120 hours.

Cells were selected by their ability to grow in (1) the above growth medium in the presence of 1 mg/ml hygromycin or (2) an IL-12 containing growth medium of RPMI 1640, 10% FBS, glutamine (2 mM), penicillin G (100 U/ml), streptomycin (100 μg/ml), and various concentrations (10, 50 or 250 ng/ml) of human IL-12.

Ba/F3 cells expressing human IL-12 beta1 receptor protein transfected with pEF-BOS plasmid DNA expressing recombinant human IL-12 beta2 receptor protein grew in the IL-12 containing growth medium, demonstrating that coexpression of human IL-12 beta1 receptor protein and human IL-12 beta2 receptor protein conferred human IL-12 responsiveness to the Ba/F3 cells.

Additionally, Ba/F3 cells expressing human IL-12 beta2 receptor protein grow in the IL-12 containing growth medium, demonstrating that expression of human IL-12 beta2 receptor protein conferred human IL-12 responsiveness to the Ba/F3 cells.

Effect of Human IL-12 on Transfected Ba/F3 Cell Lines

Ba/F3 cells (1) expressing human IL-12 beta1 receptor protein, (2) expressing human IL-12 beta2 receptor protein, or (3) coexpressing human IL-12 beta1 receptor protein and human IL-12 beta2 receptor protein were cultured in RPMI-1640 medium supplemented with 10% FBS, 100 U/ml penicillin G, 100 μg/ml streptomycin, and 2 mM L-glutamine at 2×10$^4$ cells/well in Costar 3596 flat-bottom microplates for 24 hours. Various dilutions of human IL-12, as shown in FIG. 6, were then added to the microplates and the cells were incubated for 42 hours at 37° C. in a humidified atmosphere of 5% CO$_2$ in air. 50 μl of $^3$H-thymidine, 10 μCi/ml in culture medium, was then added to each well. The cultures were further incubated for 6 hours at 37° C. Subsequently, the culture contents were harvested onto glass fiber filters by means of a cell harvester. $^3$H-thymidine incorporation was measured by use of a liquid scintillation counter. All samples were assayed in quadruplicate.

Results

Sequence Analysis of IL-12 Receptor cDNA Clones and Encoded IL-12 Receptor Protein The IL-12 beta2 receptor protein, composed of 862 amino acids and a calculated molecular weight of 97231, had the following features: N-terminal signal peptide, extracellular domain, transmembrane domain and cytoplasmic tail. The classical hydrophobic N-terminal signal peptide is predicted to be 23 amino acids in length. Signal peptide cleavage occurs mostly after the amino acids Ala, Ser, Gly, Cys, Thr, Gln (von Heijne, G., 1986, Nucl. Acids Research, 14:4683). For the IL-12 receptor, the cleavage could thus take place after Ala23 in the sequence shown in SEQ ID NO:2, leaving a mature protein of 839 amino acids based on cleavage at Ala23. The extracellular domain of the receptor is predicted to encompass the region from the C-terminus of the signal peptide to amino acid No. 622 in the sequence shown in SEQ ID NO:2. Hydrophobicity analysis shows the area from amino acid No. 623 to 646 to be hydrophobic, as would be expected for a transmembrane anchor region. Charged transfer stop residues can be found at the N- as well as the C-terminus of this predicted transmembrane area. The extracellular domain of the receptor is thus 599 amino acids long and contains 9 predicted N-linked glycosylation sites. The cytoplasmic portion is 215 amino acids long (amino acid residue nos. 647 to 862).

Further analysis of the amino acid sequence shown in SEQ ID NO:2 shows the human IL-12 beta2 receptor protein is a member of the cytokine receptor superfamily, by virtue of the sequence motifs [Cys132 - - - Cys143TW] and [W305SKWS]. Comparing the sequence shown in SEQ ID NO:2 to all the members of the superfamily by running the ALIGN program shows that the human IL-12 beta2 receptor protein has the highest homology to human gp130. The cytoplasmic region of the IL-12 receptor beta2 chain contains the box 1 and 2 motifs found in other cytokine receptor superfamily members, as well as three tyrosine residues. Phosphorylation of tyrosines is commonly associated with cytokine receptor signalling; the presence of these tyrosine residues underscores the importance of the IL-12 receptor beta2 chain in the formation of a functional IL-12 receptor. The IL-12 receptor beta1 chain does not contain any tyrosine residues in its cytoplasmic tail.

Binding Assays

We have found that human IL-12 binds to recombinant IL-12 receptor beta1 or beta2 alone with an apparent affinity of about 2–5 nM. The binding data was described by a single site receptor model, corresponding to the low affinity component of the functional IL-12 receptor found on PHA-activated PBMC (R. Chizzonite et al., 1992, J. Immunol., 148:3117; B. Desai et al., 1992, J. Immunol., 148:3125).

In contrast to these results, we conducted a both high and low affinity IL-12 binding sites were generated upon cotransfection of COS cells with IL-12 receptor beta1 and beta2 plasmids. In this case, the binding data were described by a two receptor site model, with affinities of 50 pM and 5 nM.

Effect of Human IL-12 on Transfected Ba/F3 Cell Lines

The results of the proliferation assay for the effect of human IL-12 on Ba/F3 cells (1) expressing human IL-12 beta1 receptor protein, (2) expressing human IL-12 beta2 receptor protein, and (3) coexpressing human IL-12 beta1 receptor protein and human IL-12 beta2 receptor protein.

We have found that cells that are transfected with cDNAs for both human IL-12 beta1 receptor protein and human IL-12 beta2 receptor protein respond to stimulation by human IL-12 by proliferating in a dose-dependent manner.

Additionally, cells we have found that are transfected with cDNAs for human IL-12 beta2 receptor protein respond to stimulation by human IL-12 by proliferating in a dose-dependent manner.

Conclusion

The isolated cDNA (clone No. B5-10, SEQ. ID. No:1) coding for a type I transmembrane protein represents a second component of the IL-12 receptor (IL-12R beta2) found on normal human T-cells. The beta1 and beta2 chains each alone bind IL-12 only with low affinity (Kd=2–5 nM). Upon coexpression of beta1 and beta2, two affinity sites are observed, with Kd values of 50 pM and 5 nM.

Ba/F3 cells expressing human IL-12 beta2 receptor protein or coexpressing human IL-12 beta1 receptor protein and human IL-12 beta2 receptor protein are responsive to human IL-12.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. An isolated DNA which encodes human interleukin-12 (IL-12) beta2 receptor protein and comprises a DNA sequence encoding the amino acid sequence SEQ ID NO:2 or a DNA sequence that hybridizes under stringent conditions to the nucleic acid that encodes for the amino acids of SEQ ID NO:2 which
   (a) has low binding affinity for human IL-12, and
   (b) when complexed with a human IL-12 beta1 receptor protein forms a complex having high binding affinity to human IL-12.

2. The isolated DNA of claim 1, wherein the DNA is a cDNA.

3. The isolated DNA of claim 1, having SEQ ID NO:1.

4. A non-human host cell capable of expressing on its surface human interleukin-12 (IL-12) beta2 receptor protein encoded or a DNA sequence that hybridizes under stringent conditions to the nucleic acid that encodes for the amino acids of SEQ ID No:2 which
   (a) has low binding affinity for human IL-12, and
   (b) when complexed with a human IL-12 beta1 receptor protein forms a complex having high binding affinity to human IL-12.

5. The non-human host cell of claim 4, wherein the non-human host cell is mammalian.

6. The non-human host cell of claim 4, wherein the host cell is transfected with a vector expressing a DNA encoding human IL-12 beta2 receptor protein, or the fragment thereof.

7. The non-human host cell of claim 4, wherein the isolated polynucleotide has SEQ ID NO:1.

8. The non-human host cell of claim 4, wherein the host cell proliferates in the presence of human IL-12.

9. A non-human host cell having expressed on its surface human interleukin-12 (IL-12) beta2 receptor protein encoded by a DNA sequence which encodes the amino acid sequence SEQ ID NO:2 or a DNA sequence that hybridizes under stringent conditions to the nucleic acid that encodes for the amino acids of SEQ ID NO:2 which (a) has low binding affinity for human IL-12, and (b) when complexed with a human IL-12 beta1 receptor protein forms a complex having high binding affinity to human IL-12.

10. The non-human host cell of claim 9, wherein the non-human host cell is mammalian.

11. The non-human host cell of claim 9, wherein the isolated polynucleotide has SEQ ID NO:1.

12. The non-human host cell of claim 9, wherein the host cell proliferates in the presence of human IL-12.

* * * * *

UNITED STATES PATENT AND TRADEMARK OFFICE
CERTIFICATE OF CORRECTION

PATENT NO. : 5,840,530
DATED : Nov. 24, 1998
INVENTOR(S) : Gubler, et al.

It is certified that error appears in the above-identified patent and that said Letters Patent is hereby corrected as shown below:

Title page, insert the following:

--Related U.S. Application Data
[60] Provisional application No. 60/001,701, Aug. 1, 1995, and provisional application No. 60/018,674, May 30, 1996.--

Column 1, lines 5-7, should be deleted to read as follows:

--CROSS REFERENCE TO RELATED APPLICATION
Reference is made to U.S. Provisional application Ser. No. US 60/001,701, filed Aug. 1, 1995, and US 60/018,674, filed May 30, 1996, entitled RECEPTORS FOR HUMAN INTERLEUKIN-12.--

Signed and Sealed this

Thirteenth Day of April, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4040 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 641..3226

( x i ) SEQUENCE DESCRIPTION: SEQ ID NO:1:

```
TGCAGAGAAC   AGAGAAAGGA   CATCTGCGAG   GAAAGTTCCC   TGATGGCTGT   CAACAAAGTG        60

CCACGTCTCT   ATGGCTGTGT   ACGCTGAGCA   CACGATTTTA   TCGCGCCTAT   CATATCTTGG       120

TGCATAAACG   CACCTCACCT   CGGTCAACCC   TTGCTCCGTC   TTATGAGACA   GGCTTTATTA       180
```

```
TCCGCATTTT ATATGAGGGG AATCTGACGG TGGAGAGAGA ATTATCTTGC TCAAGGCGAC        240

ACAGCAGAGC CCACAGGTGG CAGAATCCCA CCCGAGCCCG CTTCGACCCG CGGGGTGGAA        300

ACCACGGGCG CCCGCCCGGC TGCGCTTCCA GAGCTGAACT GAGAAGCGAG TCCTCTCCGC        360

CCTGCGGCCA CCGCCCAGCC CCGACCCCCG CCCCGGCCCG ATCCTCACTC GCCGCCAGCT        420

CCCCGCGCCC ACCCCGGAGT TGGTGGCGCA GAGGCGGGAG GCGGAGGCGG GAGGCGGGC         480

GCTGGCACCG GGAACGCCCG AGCGCCGGCA GAGAGCGCGG AGAGCGCGAC ACGTGCGGCC        540

CAGAGCACCG GGGCCACCCG GTCCCCGCAG GCCCGGGACC GCGCCCGCTG GCAGGCGACA        600

CGTGGAAGAA TACGGAGTTC TATACCAGAG TTGATTGTTG ATG GCA CAT ACT TTT         655
                                              Met Ala His Thr Phe
                                                1                 5

AGA GGA TGC TCA TTG GCA TTT ATG TTT ATA ATC ACG TGG CTG TTG ATT         703
Arg Gly Cys Ser Leu Ala Phe Met Phe Ile Ile Thr Trp Leu Leu Ile
            10                  15                  20

AAA GCA AAA ATA GAT GCG TGC AAG AGA GGC GAT GTG ACT GTG AAG CCT         751
Lys Ala Lys Ile Asp Ala Cys Lys Arg Gly Asp Val Thr Val Lys Pro
                25                  30                  35

TCC CAT GTA ATT TTA CTT GGA TCC ACT GTC AAT ATT ACA TGC TCT TTG         799
Ser His Val Ile Leu Leu Gly Ser Thr Val Asn Ile Thr Cys Ser Leu
        40                  45                  50

AAG CCC AGA CAA GGC TGC TTT CAC TAT TCC AGA CGT AAC AAG TTA ATC         847
Lys Pro Arg Gln Gly Cys Phe His Tyr Ser Arg Arg Asn Lys Leu Ile
    55                  60                  65

CTG TAC AAG TTT GAC AGA AGA ATC AAT TTT CAC CAT GGC CAC TCC CTC         895
Leu Tyr Lys Phe Asp Arg Arg Ile Asn Phe His His Gly His Ser Leu
70                  75                  80                      85

AAT TCT CAA GTC ACA GGT CTT CCC CTT GGT ACA ACC TTG TTT GTC TGC         943
Asn Ser Gln Val Thr Gly Leu Pro Leu Gly Thr Thr Leu Phe Val Cys
                    90                  95                  100

AAA CTG GCC TGT ATC AAT AGT GAT GAA ATT CAA ATA TGT GGA GCA GAG         991
Lys Leu Ala Cys Ile Asn Ser Asp Glu Ile Gln Ile Cys Gly Ala Glu
                105                 110                 115

ATC TTC GTT GGT GTT GCT CCA GAA CAG CCT CAA AAT TTA TCC TGC ATA         1039
Ile Phe Val Gly Val Ala Pro Glu Gln Pro Gln Asn Leu Ser Cys Ile
            120                 125                 130

CAG AAG GGA GAA CAG GGG ACT GTG GCC TGC ACC TGG GAA AGA GGA CGA         1087
Gln Lys Gly Glu Gln Gly Thr Val Ala Cys Thr Trp Glu Arg Gly Arg
135                 140                 145

GAC ACC CAC TTA TAC ACT GAG TAT ACT CTA CAG CTA AGT GGA CCA AAA         1135
Asp Thr His Leu Tyr Thr Glu Tyr Thr Leu Gln Leu Ser Gly Pro Lys
150                 155                 160                 165

AAT TTA ACC TGG CAG AAG CAA TGT AAA GAC ATT TAT TGT GAC TAT TTG         1183
Asn Leu Thr Trp Gln Lys Gln Cys Lys Asp Ile Tyr Cys Asp Tyr Leu
                170                 175                 180

GAC TTT GGA ATC AAC CTC ACC CCT GAA TCA CCT GAA TCC AAT TTC ACA         1231
Asp Phe Gly Ile Asn Leu Thr Pro Glu Ser Pro Glu Ser Asn Phe Thr
            185                 190                 195

GCC AAG GTT ACT GCT GTC AAT AGT CTT GGA AGC TCC TCT TCA CTT CCA         1279
Ala Lys Val Thr Ala Val Asn Ser Leu Gly Ser Ser Ser Ser Leu Pro
        200                 205                 210

TCC ACA TTC ACA TTC TTG GAC ATA GTG AGG CCT CTT CCT CCG TGG GAC         1327
Ser Thr Phe Thr Phe Leu Asp Ile Val Arg Pro Leu Pro Pro Trp Asp
215                 220                 225

ATT AGA ATC AAA TTT CAA AAG GCT TCC GTG AGC AGA TGT ACC CTT TAT         1375
Ile Arg Ile Lys Phe Gln Lys Ala Ser Val Ser Arg Cys Thr Leu Tyr
230                 235                 240                 245

TGG AGA GAT GAG GGA CTG GTA CTG CTT AAT CGA CTC AGA TAT CGG CCC         1423
Trp Arg Asp Glu Gly Leu Val Leu Leu Asn Arg Leu Arg Tyr Arg Pro
```

-continued

|  |  |  |  |  | 250 |  |  |  |  | 255 |  |  |  |  | 260 |  |
|---|---|---|---|---|---|---|---|---|---|---|---|---|---|---|---|---|
| AGT | AAC | AGC | AGG | CTC | TGG | AAT | ATG | GTT | AAT | GTT | ACA | AAG | GCC | AAA | GGA | 1471 |
| Ser | Asn | Ser | Arg 265 | Leu | Trp | Asn | Met | Val 270 | Asn | Val | Thr | Lys | Ala 275 | Lys | Gly |  |
| AGA | CAT | GAT | TTG | CTG | GAT | CTG | AAA | CCA | TTT | ACA | GAA | TAT | GAA | TTT | CAG | 1519 |
| Arg | His | Asp 280 | Leu | Leu | Asp | Leu | Lys 285 | Pro | Phe | Thr | Glu | Tyr 290 | Glu | Phe | Gln |  |
| ATT | TCC | TCT | AAG | CTA | CAT | CTT | TAT | AAG | GGA | AGT | TGG | AGT | GAT | TGG | AGT | 1567 |
| Ile | Ser 295 | Ser | Lys | Leu | His 300 | Leu | Tyr | Lys | Gly | Ser | Trp 305 | Ser | Asp | Trp | Ser |  |
| GAA | TCA | TTG | AGA | GCA | CAA | ACA | CCA | GAA | GAA | GAG | CCT | ACT | GGG | ATG | TTA | 1615 |
| Glu 310 | Ser | Leu | Arg | Ala | Gln 315 | Thr | Pro | Glu | Glu | Glu 320 | Pro | Thr | Gly | Met | Leu 325 |  |
| GAT | GTC | TGG | TAC | ATG | AAA | CGG | CAC | ATT | GAC | TAC | AGT | AGA | CAA | CAG | ATT | 1663 |
| Asp | Val | Trp | Tyr | Met 330 | Lys | Arg | His | Ile | Asp 335 | Tyr | Ser | Arg | Gln | Gln 340 | Ile |  |
| TCT | CTT | TTC | TGG | AAG | AAT | CTG | AGT | GTC | TCA | GAG | GCA | AGA | GGA | AAA | ATT | 1711 |
| Ser | Leu | Phe | Trp 345 | Lys | Asn | Leu | Ser | Val 350 | Ser | Glu | Ala | Arg | Gly 355 | Lys | Ile |  |
| CTC | CAC | TAT | CAG | GTG | ACC | TTG | CAG | GAG | CTG | ACA | GGA | GGG | AAA | GCC | ATG | 1759 |
| Leu | His | Tyr 360 | Gln | Val | Thr | Leu | Gln 365 | Glu | Leu | Thr | Gly | Gly 370 | Lys | Ala | Met |  |
| ACA | CAG | AAC | ATC | ACA | GGA | CAC | ACC | TCC | TGG | ACC | ACA | GTC | ATT | CCT | AGA | 1807 |
| Thr | Gln | Asn 375 | Ile | Thr | Gly | His 380 | Thr | Ser | Trp | Thr | Thr 385 | Val | Ile | Pro | Arg |  |
| ACC | GGA | AAT | TGG | GCT | GTG | GCT | GTG | TCT | GCA | GCA | AAT | TCA | AAA | GGC | AGT | 1855 |
| Thr 390 | Gly | Asn | Trp | Ala | Val 395 | Ala | Val | Ser | Ala | Ala 400 | Asn | Ser | Lys | Gly | Ser 405 |  |
| TCT | CTG | CCC | ACT | CGT | ATT | AAC | ATA | ATG | AAC | CTG | TGT | GAG | GCA | GGG | TTG | 1903 |
| Ser | Leu | Pro | Thr | Arg 410 | Ile | Asn | Ile | Met | Asn 415 | Leu | Cys | Glu | Ala | Gly 420 | Leu |  |
| CTG | GCT | CCT | CGC | CAG | GTC | TCT | GCA | AAC | TCA | GAG | GGC | ATG | GAC | AAC | ATT | 1951 |
| Leu | Ala | Pro | Arg 425 | Gln | Val | Ser | Ala | Asn 430 | Ser | Glu | Gly | Met | Asp 435 | Asn | Ile |  |
| CTG | GTG | ACT | TGG | CAG | CCT | CCC | AGG | AAA | GAT | CCC | TCT | GCT | GTT | CAG | GAG | 1999 |
| Leu | Val | Thr 440 | Trp | Gln | Pro | Pro | Arg 445 | Lys | Asp | Pro | Ser | Ala 450 | Val | Gln | Glu |  |
| TAC | GTG | GTG | GAA | TGG | AGA | GAG | CTC | CAT | CCA | GGG | GGT | GAC | ACA | CAG | GTC | 2047 |
| Tyr | Val | Val 455 | Glu | Trp | Arg | Glu 460 | Leu | His | Pro | Gly | Gly 465 | Asp | Thr | Gln | Val |  |
| CCT | CTA | AAC | TGG | CTA | CGG | AGT | CGA | CCC | TAC | AAT | GTG | TCT | GCT | CTG | ATT | 2095 |
| Pro 470 | Leu | Asn | Trp | Leu | Arg 475 | Ser | Arg | Pro | Tyr | Asn 480 | Val | Ser | Ala | Leu | Ile 485 |  |
| TCA | GAG | AAC | ATA | AAA | TCC | TAC | ATC | TGT | TAT | GAA | ATC | CGT | GTG | TAT | GCA | 2143 |
| Ser | Glu | Asn | Ile | Lys 490 | Ser | Tyr | Ile | Cys | Tyr 495 | Glu | Ile | Arg | Val | Tyr 500 | Ala |  |
| CTC | TCA | GGG | GAT | CAA | GGA | GGA | TGC | AGC | TCC | ATC | CTG | GGT | AAC | TCT | AAG | 2191 |
| Leu | Ser | Gly | Asp 505 | Gln | Gly | Gly | Cys | Ser 510 | Ser | Ile | Leu | Gly | Asn 515 | Ser | Lys |  |
| CAC | AAA | GCA | CCA | CTG | AGT | GGC | CCC | CAC | ATT | AAT | GCC | ATC | ACA | GAG | GAA | 2239 |
| His | Lys | Ala 520 | Pro | Leu | Ser | Gly | Pro 525 | His | Ile | Asn | Ala | Ile 530 | Thr | Glu | Glu |  |
| AAG | GGG | AGC | ATT | TTA | ATT | TCA | TGG | AAC | AGC | ATT | CCA | GTC | CAG | GAG | CAA | 2287 |
| Lys | Gly | Ser 535 | Ile | Leu | Ile | Ser | Trp 540 | Asn | Ser | Ile | Pro | Val 545 | Gln | Glu | Gln |  |
| ATG | GGC | TGC | CTC | CTC | CAT | TAT | AGG | ATA | TAC | TGG | AAG | GAA | CGG | GAC | TCC | 2335 |
| Met | Gly | Cys | Leu | Leu 555 | His | Tyr | Arg | Ile | Tyr 560 | Trp | Lys | Glu | Arg | Asp 565 | Ser |  |
| AAC | TCC | CAG | CCT | CAG | CTC | TGT | GAA | ATT | CCC | TAC | AGA | GTC | TCC | CAA | AAT | 2383 |
| Asn | Ser | Gln | Pro | Gln | Leu | Cys | Glu | Ile | Pro | Tyr | Arg | Val | Ser | Gln | Asn |  |

-continued

|  |  |  |  |  |  |  |  |  |  |  |  |  |  |  |  |  |
|---|---|---|---|---|---|---|---|---|---|---|---|---|---|---|---|---|
|  |  |  |  |  | 570 |  |  |  |  | 575 |  |  |  |  | 580 |  |
| TCA | CAT | CCA | ATA | AAC | AGC | CTG | CAG | CCC | CGA | GTG | ACA | TAT | GTC | CTG | TGG | 2431 |
| Ser | His | Pro | Ile | Asn | Ser | Leu | Gln | Pro | Arg | Val | Thr | Tyr | Val | Leu | Trp |  |
|  |  |  | 585 |  |  |  |  | 590 |  |  |  |  | 595 |  |  |  |
| ATG | ACA | GCT | CTG | ACA | GCT | GCT | GGT | GAA | AGT | TCC | CAC | GGA | AAT | GAG | AGG | 2479 |
| Met | Thr | Ala | Leu | Thr | Ala | Ala | Gly | Glu | Ser | Ser | His | Gly | Asn | Glu | Arg |  |
|  | 600 |  |  |  |  | 605 |  |  |  |  | 610 |  |  |  |  |  |
| GAA | TTT | TGT | CTG | CAA | GGT | AAA | GCC | AAT | TGG | ATG | GCG | TTT | GTG | GCA | CCA | 2527 |
| Glu | Phe | Cys | Leu | Gln | Gly | Lys | Ala | Asn | Trp | Met | Ala | Phe | Val | Ala | Pro |  |
|  | 615 |  |  |  | 620 |  |  |  |  | 625 |  |  |  |  |  |  |
| AGC | ATT | TGC | ATT | GCT | ATC | ATC | ATG | GTG | GGC | ATT | TTC | TCA | ACG | CAT | TAC | 2575 |
| Ser | Ile | Cys | Ile | Ala | Ile | Ile | Met | Val | Gly | Ile | Phe | Ser | Thr | His | Tyr |  |
| 630 |  |  |  |  | 635 |  |  |  |  | 640 |  |  |  |  | 645 |  |
| TTC | CAG | CAA | AAG | GTG | TTT | GTT | CTC | CTA | GCA | GCC | CTC | AGA | CCT | CAG | TGG | 2623 |
| Phe | Gln | Gln | Lys | Val | Phe | Val | Leu | Leu | Ala | Ala | Leu | Arg | Pro | Gln | Trp |  |
|  |  |  |  | 650 |  |  |  |  | 655 |  |  |  |  | 660 |  |  |
| TGT | AGC | AGA | GAA | ATT | CCA | GAT | CCA | GCA | AAT | AGC | ACT | TGC | GCT | AAG | AAA | 2671 |
| Cys | Ser | Arg | Glu | Ile | Pro | Asp | Pro | Ala | Asn | Ser | Thr | Cys | Ala | Lys | Lys |  |
|  |  |  | 665 |  |  |  |  | 670 |  |  |  |  | 675 |  |  |  |
| TAT | CCC | ATT | GCA | GAG | GAG | AAG | ACA | CAG | CTG | CCC | TTG | GAC | AGG | CTC | CTG | 2719 |
| Tyr | Pro | Ile | Ala | Glu | Glu | Lys | Thr | Gln | Leu | Pro | Leu | Asp | Arg | Leu | Leu |  |
|  |  | 680 |  |  |  |  | 685 |  |  |  |  | 690 |  |  |  |  |
| ATA | GAC | TGG | CCC | ACG | CCT | GAA | GAT | CCT | GAA | CCG | CTG | GTC | ATC | AGT | GAA | 2767 |
| Ile | Asp | Trp | Pro | Thr | Pro | Glu | Asp | Pro | Glu | Pro | Leu | Val | Ile | Ser | Glu |  |
|  | 695 |  |  |  |  | 700 |  |  |  |  | 705 |  |  |  |  |  |
| GTC | CTT | CAT | CAA | GTG | ACC | CCA | GTT | TTC | AGA | CAT | CCC | CCC | TGC | TCC | AAC | 2815 |
| Val | Leu | His | Gln | Val | Thr | Pro | Val | Phe | Arg | His | Pro | Pro | Cys | Ser | Asn |  |
| 710 |  |  |  |  | 715 |  |  |  |  | 720 |  |  |  |  | 725 |  |
| TGG | CCA | CAA | AGG | GAA | AAA | GGA | ATC | CAA | GGT | CAT | CAG | GCC | TCT | GAG | AAA | 2863 |
| Trp | Pro | Gln | Arg | Glu | Lys | Gly | Ile | Gln | Gly | His | Gln | Ala | Ser | Glu | Lys |  |
|  |  |  |  | 730 |  |  |  |  | 735 |  |  |  |  | 740 |  |  |
| GAC | ATG | ATG | CAC | AGT | GCC | TCA | AGC | CCA | CCA | CCT | CCA | AGA | GCT | CTC | CAA | 2911 |
| Asp | Met | Met | His | Ser | Ala | Ser | Ser | Pro | Pro | Pro | Pro | Arg | Ala | Leu | Gln |  |
|  |  |  | 745 |  |  |  |  | 750 |  |  |  |  | 755 |  |  |  |
| GCT | GAG | AGC | AGA | CAA | CTG | GTG | GAT | CTG | TAC | AAG | GTG | CTG | GAG | AGC | AGG | 2959 |
| Ala | Glu | Ser | Arg | Gln | Leu | Val | Asp | Leu | Tyr | Lys | Val | Leu | Glu | Ser | Arg |  |
|  |  | 760 |  |  |  |  | 765 |  |  |  |  | 770 |  |  |  |  |
| GGC | TCC | GAC | CCA | AAG | CCA | GAA | AAC | CCA | GCC | TGT | CCC | TGG | ACG | GTG | CTC | 3007 |
| Gly | Ser | Asp | Pro | Lys | Pro | Glu | Asn | Pro | Ala | Cys | Pro | Trp | Thr | Val | Leu |  |
|  | 775 |  |  |  |  | 780 |  |  |  |  | 785 |  |  |  |  |  |
| CCA | GCA | GGT | GAC | CTT | CCC | ACC | CAT | GAT | GGC | TAC | TTA | CCC | TCC | AAC | ATA | 3055 |
| Pro | Ala | Gly | Asp | Leu | Pro | Thr | His | Asp | Gly | Tyr | Leu | Pro | Ser | Asn | Ile |  |
| 790 |  |  |  |  | 795 |  |  |  |  | 800 |  |  |  |  | 805 |  |
| GAT | GAC | CTC | CCC | TCA | CAT | GAG | GCA | CCT | CTC | GCT | GAC | TCT | CTG | GAA | GAA | 3103 |
| Asp | Asp | Leu | Pro | Ser | His | Glu | Ala | Pro | Leu | Ala | Asp | Ser | Leu | Glu | Glu |  |
|  |  |  |  | 810 |  |  |  |  | 815 |  |  |  |  | 820 |  |  |
| CTG | GAG | CCT | CAG | CAC | ATC | TCC | CTT | TCT | GTT | TTC | CCC | TCA | AGT | TCT | CTT | 3151 |
| Leu | Glu | Pro | Gln | His | Ile | Ser | Leu | Ser | Val | Phe | Pro | Ser | Ser | Ser | Leu |  |
|  |  |  | 825 |  |  |  |  | 830 |  |  |  |  | 835 |  |  |  |
| CAC | CCA | CTC | ACC | TTC | TCC | TGT | GGT | GAT | AAG | CTG | ACT | CTG | GAT | CAG | TTA | 3199 |
| His | Pro | Leu | Thr | Phe | Ser | Cys | Gly | Asp | Lys | Leu | Thr | Leu | Asp | Gln | Leu |  |
|  |  | 840 |  |  |  |  | 845 |  |  |  |  | 850 |  |  |  |  |
| AAG | ATG | AGG | TGT | GAC | TCC | CTC | ATG | CTC | TGAGTGGTGA | GGCTTCAAGC |  |  |  |  |  | 3246 |
| Lys | Met | Arg | Cys | Asp | Ser | Leu | Met | Leu |  |  |  |  |  |  |  |  |
|  | 855 |  |  |  |  | 860 |  |  |  |  |  |  |  |  |  |  |
| CTTAAAGTCA | GTGTGCCCTC | AACCAGCACA | GCCTGCCCCA | ATTCCCCCAG | CCCCTGCTCC |  |  |  |  |  |  |  |  |  |  | 3306 |
| AGCAGCTGTC | ATCTCTGGGT | GCCACCATCG | GTCTGGCTGC | AGCTAGAGGA | CAGGCAAGCC |  |  |  |  |  |  |  |  |  |  | 3366 |
| AGCTCTGGGG | GAGTCTTAGG | AACTGGGAGT | TGGTCTTCAC | TCAGATGCCT | CATCTTGCCT |  |  |  |  |  |  |  |  |  |  | 3426 |

|  |  |  |  |  |  |
|---|---|---|---|---|---|
| TTCCCAGGGC | CTTAAAATTA | CATCCTTCAC | TGTGTGGACC | TAGAGACTCC | AACTTGAATT | 3486
| CCTAGTAACT | TTCTTGGTAT | GCTGGCCAGA | AAGGGAAATG | AGGAGGAGAG | TAGAAACCAC | 3546
| AGCTCTTAGT | AGTAATGGCA | TACAGTCTAG | AGGACCATTC | ATGCAATGAC | TATTTCTAAA | 3606
| GCACCTGCTA | CACAGCAGGC | TGTACACAGC | AGATCAGTAC | TGTTCAACAG | AACTTCCTGA | 3666
| GATGATGGAA | ATGTTCTACC | TCTGCACTCA | CTGTCCAGTA | CATTAGACAC | TAGGCACATT | 3726
| GGCTGTTAAT | CACTTGGAAT | GTGTTTAGCT | TGACTGAGGA | ATTAAATTTT | GATTGTAAAT | 3786
| TTAAATCGCC | ACACATGGCT | AGTGGCTACT | GTATTGGAGT | GCACAGCTCT | AGATGGCTCC | 3846
| TAGATTATTG | AGAGCCTCCA | AAACAAATCA | ACCTAGTTCT | ATAGATGAAG | ACATAAAAGA | 3906
| CACTGGTAAA | CACCAATGTA | AAAGGGCCCC | CAAGGTGGTC | ATGACTGGTC | TCATTTGCAG | 3966
| AAGTCTAAGA | ATGTACCTTT | TTCTGGCCGG | GCGTGGTAGC | TCATGCCTGT | AATCCCAGCA | 4026
| CTTTGGGAGG | CTGA |  |  |  |  | 4040

(2) INFORMATION FOR SEQ ID NO:2:

(i) SEQUENCE CHARACTERISTICS:
        (A) LENGTH: 862 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Ala  His  Thr  Phe  Arg  Gly  Cys  Ser  Leu  Ala  Phe  Met  Phe  Ile  Ile
  1                   5                  10                  15

Thr  Trp  Leu  Leu  Ile  Lys  Ala  Lys  Ile  Asp  Ala  Cys  Lys  Arg  Gly  Asp
             20                  25                  30

Val  Thr  Val  Lys  Pro  Ser  His  Val  Ile  Leu  Leu  Gly  Ser  Thr  Val  Asn
         35                  40                  45

Ile  Thr  Cys  Ser  Leu  Lys  Pro  Arg  Gln  Gly  Cys  Phe  His  Tyr  Ser  Arg
     50                  55                  60

Arg  Asn  Lys  Leu  Ile  Leu  Tyr  Lys  Phe  Asp  Arg  Arg  Ile  Asn  Phe  His
 65                  70                  75                  80

His  Gly  His  Ser  Leu  Asn  Ser  Gln  Val  Thr  Gly  Leu  Pro  Leu  Gly  Thr
                 85                  90                  95

Thr  Leu  Phe  Val  Cys  Lys  Leu  Ala  Cys  Ile  Asn  Ser  Asp  Glu  Ile  Gln
            100                 105                 110

Ile  Cys  Gly  Ala  Glu  Ile  Phe  Val  Gly  Val  Ala  Pro  Glu  Gln  Pro  Gln
         115                 120                 125

Asn  Leu  Ser  Cys  Ile  Gln  Lys  Gly  Glu  Gln  Gly  Thr  Val  Ala  Cys  Thr
     130                 135                 140

Trp  Glu  Arg  Gly  Arg  Asp  Thr  His  Leu  Tyr  Thr  Glu  Tyr  Thr  Leu  Gln
145                 150                 155                 160

Leu  Ser  Gly  Pro  Lys  Asn  Leu  Thr  Trp  Gln  Lys  Gln  Cys  Lys  Asp  Ile
                 165                 170                 175

Tyr  Cys  Asp  Tyr  Leu  Asp  Phe  Gly  Ile  Asn  Leu  Thr  Pro  Glu  Ser  Pro
            180                 185                 190

Glu  Ser  Asn  Phe  Thr  Ala  Lys  Val  Thr  Ala  Val  Asn  Ser  Leu  Gly  Ser
         195                 200                 205

Ser  Ser  Ser  Leu  Pro  Ser  Thr  Phe  Thr  Phe  Leu  Asp  Ile  Val  Arg  Pro
     210                 215                 220

Leu  Pro  Pro  Trp  Asp  Ile  Arg  Ile  Lys  Phe  Gln  Lys  Ala  Ser  Val  Ser
225                 230                 235                 240

Arg  Cys  Thr  Leu  Tyr  Trp  Arg  Asp  Glu  Gly  Leu  Val  Leu  Leu  Asn  Arg
```

-continued

|     |     |     | 245 |     |     |     |     | 250 |     |     |     |     | 255 |     |
|-----|-----|-----|-----|-----|-----|-----|-----|-----|-----|-----|-----|-----|-----|-----|

Leu Arg Tyr Arg Pro Ser Asn Ser Leu Trp Asn Met Val Asn Val
                260             265             270

Thr Lys Ala Lys Gly Arg His Asp Leu Leu Asp Leu Lys Pro Phe Thr
        275             280             285

Glu Tyr Glu Phe Gln Ile Ser Ser Lys Leu His Leu Tyr Lys Gly Ser
    290             295             300

Trp Ser Asp Trp Ser Glu Ser Leu Arg Ala Gln Thr Pro Glu Glu Glu
305             310             315             320

Pro Thr Gly Met Leu Asp Val Trp Tyr Met Lys Arg His Ile Asp Tyr
                325             330             335

Ser Arg Gln Gln Ile Ser Leu Phe Trp Lys Asn Leu Ser Val Ser Glu
                340             345             350

Ala Arg Gly Lys Ile Leu His Tyr Gln Val Thr Leu Gln Glu Leu Thr
                355             360             365

Gly Gly Lys Ala Met Thr Gln Asn Ile Thr Gly His Thr Ser Trp Thr
    370             375             380

Thr Val Ile Pro Arg Thr Gly Asn Trp Ala Val Ala Val Ser Ala Ala
385             390             395             400

Asn Ser Lys Gly Ser Ser Leu Pro Thr Arg Ile Asn Ile Met Asn Leu
                405             410             415

Cys Glu Ala Gly Leu Leu Ala Pro Arg Gln Val Ser Ala Asn Ser Glu
                420             425             430

Gly Met Asp Asn Ile Leu Val Thr Trp Gln Pro Pro Arg Lys Asp Pro
            435             440             445

Ser Ala Val Gln Glu Tyr Val Val Glu Trp Arg Glu Leu His Pro Gly
    450             455             460

Gly Asp Thr Gln Val Pro Leu Asn Trp Leu Arg Ser Arg Pro Tyr Asn
465             470             475             480

Val Ser Ala Leu Ile Ser Glu Asn Ile Lys Ser Tyr Ile Cys Tyr Glu
                485             490             495

Ile Arg Val Tyr Ala Leu Ser Gly Asp Gln Gly Gly Cys Ser Ser Ile
            500             505             510

Leu Gly Asn Ser Lys His Lys Ala Pro Leu Ser Gly Pro His Ile Asn
        515             520             525

Ala Ile Thr Glu Glu Lys Gly Ser Ile Leu Ile Ser Trp Asn Ser Ile
    530             535             540

Pro Val Gln Glu Gln Met Gly Cys Leu Leu His Tyr Arg Ile Tyr Trp
545             550             555             560

Lys Glu Arg Asp Ser Asn Ser Gln Pro Gln Leu Cys Glu Ile Pro Tyr
                565             570             575

Arg Val Ser Gln Asn Ser His Pro Ile Asn Ser Leu Gln Pro Arg Val
                580             585             590

Thr Tyr Val Leu Trp Met Thr Ala Leu Thr Ala Ala Gly Glu Ser Ser
        595             600             605

His Gly Asn Glu Arg Glu Phe Cys Leu Gln Gly Lys Ala Asn Trp Met
    610             615             620

Ala Phe Val Ala Pro Ser Ile Cys Ile Ala Ile Ile Met Val Gly Ile
625             630             635             640

Phe Ser Thr His Tyr Phe Gln Gln Lys Val Phe Val Leu Leu Ala Ala
                645             650             655

Leu Arg Pro Gln Trp Cys Ser Arg Glu Ile Pro Asp Pro Ala Asn Ser
            660             665             670

| Thr | Cys | Ala | Lys | Lys | Tyr | Pro | Ile | Ala | Glu | Glu | Lys | Thr | Gln | Leu | Pro |
|-----|-----|-----|-----|-----|-----|-----|-----|-----|-----|-----|-----|-----|-----|-----|-----|
|     |     | 675 |     |     |     |     | 680 |     |     |     |     | 685 |     |     |     |

| Leu | Asp | Arg | Leu | Leu | Ile | Asp | Trp | Pro | Thr | Pro | Glu | Asp | Pro | Glu | Pro |
|-----|-----|-----|-----|-----|-----|-----|-----|-----|-----|-----|-----|-----|-----|-----|-----|
|     | 690 |     |     |     |     | 695 |     |     |     | 700 |     |     |     |     |     |

| Leu | Val | Ile | Ser | Glu | Val | Leu | His | Gln | Val | Thr | Pro | Val | Phe | Arg | His |
|-----|-----|-----|-----|-----|-----|-----|-----|-----|-----|-----|-----|-----|-----|-----|-----|
| 705 |     |     |     |     | 710 |     |     |     |     | 715 |     |     |     |     | 720 |

| Pro | Pro | Cys | Ser | Asn | Trp | Pro | Gln | Arg | Glu | Lys | Gly | Ile | Gln | Gly | His |
|-----|-----|-----|-----|-----|-----|-----|-----|-----|-----|-----|-----|-----|-----|-----|-----|
|     |     |     |     | 725 |     |     |     |     | 730 |     |     |     |     | 735 |     |

| Gln | Ala | Ser | Glu | Lys | Asp | Met | Met | His | Ser | Ala | Ser | Ser | Pro | Pro | Pro |
|-----|-----|-----|-----|-----|-----|-----|-----|-----|-----|-----|-----|-----|-----|-----|-----|
|     |     |     | 740 |     |     |     |     | 745 |     |     |     |     | 750 |     |     |

| Pro | Arg | Ala | Leu | Gln | Ala | Glu | Ser | Arg | Gln | Leu | Val | Asp | Leu | Tyr | Lys |
|-----|-----|-----|-----|-----|-----|-----|-----|-----|-----|-----|-----|-----|-----|-----|-----|
|     |     | 755 |     |     |     |     | 760 |     |     |     |     | 765 |     |     |     |

| Val | Leu | Glu | Ser | Arg | Gly | Ser | Asp | Pro | Lys | Pro | Glu | Asn | Pro | Ala | Cys |
|-----|-----|-----|-----|-----|-----|-----|-----|-----|-----|-----|-----|-----|-----|-----|-----|
|     | 770 |     |     |     |     | 775 |     |     |     |     | 780 |     |     |     |     |

| Pro | Trp | Thr | Val | Leu | Pro | Ala | Gly | Asp | Leu | Pro | Thr | His | Asp | Gly | Tyr |
|-----|-----|-----|-----|-----|-----|-----|-----|-----|-----|-----|-----|-----|-----|-----|-----|
| 785 |     |     |     |     | 790 |     |     |     |     | 795 |     |     |     |     | 800 |

| Leu | Pro | Ser | Asn | Ile | Asp | Asp | Leu | Pro | Ser | His | Glu | Ala | Pro | Leu | Ala |
|-----|-----|-----|-----|-----|-----|-----|-----|-----|-----|-----|-----|-----|-----|-----|-----|
|     |     |     |     | 805 |     |     |     |     | 810 |     |     |     |     | 815 |     |

| Asp | Ser | Leu | Glu | Glu | Leu | Glu | Pro | Gln | His | Ile | Ser | Leu | Ser | Val | Phe |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |

| Pro | Ser | Ser | Ser | Leu | His | Pro | Leu | Thr | Phe | Ser | Cys | Gly | Asp | Lys | Leu |
|-----|-----|-----|-----|-----|-----|-----|-----|-----|-----|-----|-----|-----|-----|-----|-----|
|     |     | 835 |     |     |     |     | 840 |     |     |     |     | 845 |     |     |     |

| Thr | Leu | Asp | Gln | Leu | Lys | Met | Arg | Cys | Asp | Ser | Leu | Met | Leu |
|-----|-----|-----|-----|-----|-----|-----|-----|-----|-----|-----|-----|-----|-----|
|     | 850 |     |     |     |     | 855 |     |     |     |     | 860 |     |     |

( 2 ) INFORMATION FOR SEQ ID NO:3:

( i ) SEQUENCE CHARACTERISTICS:
        ( A ) LENGTH: 2104 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Homo sapiens
        ( G ) CELL TYPE: human T-cells ( v i i ) IMMEDIATE SOURCE:
        ( A ) LIBRARY: library 3 day PHA/pEF- BOS
        ( B ) CLONE: human interleukin-12 receptor clone #5

( i x ) FEATURE:
        ( A ) NAME/KEY: CDS
        ( B ) LOCATION: 65..2050

( x i ) SEQUENCE DESCRIPTION: SEQ ID NO:3:

```
GGTGGCTGAA  CCTCGCAGGT  GGCAGAGAGG  CTCCCCTGGG  GCTGTGGGGC  TCTACGTGGA        60

TCCG ATG GAG CCG CTG GTG ACC TGG GTG GTC CCC CTC CTC TTC CTC TTC            109
     Met Glu Pro Leu Val Thr Trp Val Val Pro Leu Leu Phe Leu Phe
       1               5                  10                  15

CTG CTG TCC AGG CAG GGC GCT GCC TGC AGA ACC AGT GAG TGC TGT TTT            157
Leu Leu Ser Arg Gln Gly Ala Ala Cys Arg Thr Ser Glu Cys Cys Phe
                20                  25                  30

CAG GAC CCG CCA TAT CCG GAT GCA GAC TCA GGC TCG GCC TCG GGC CCT            205
Gln Asp Pro Pro Tyr Pro Asp Ala Asp Ser Gly Ser Ala Ser Gly Pro
             35                  40                  45

AGG GAC CTG AGA TGC TAT CGG ATA TCC AGT GAT CGT TAC GAG TGC TCC            253
Arg Asp Leu Arg Cys Tyr Arg Ile Ser Ser Asp Arg Tyr Glu Cys Ser
         50                  55                  60
```

| | | | | | | | | | | | | | | | | |
|---|---|---|---|---|---|---|---|---|---|---|---|---|---|---|---|---|
| TGG | CAG | TAT | GAG | GGT | CCC | ACA | GCT | GGG | GTC | AGC | CAC | TTC | CTG | CGG | TGT | 301 |
| Trp | Gln | Tyr | Glu | Gly | Pro | Thr | Ala | Gly | Val | Ser | His | Phe | Leu | Arg | Cys | |
| | | | 65 | | | 70 | | | | 75 | | | | | | |
| TGC | CTT | AGC | TCC | GGG | CGC | TGC | TGC | TAC | TTC | GCC | GCC | GGC | TCA | GCC | ACC | 349 |
| Cys | Leu | Ser | Ser | Gly | Arg | Cys | Cys | Tyr | Phe | Ala | Ala | Gly | Ser | Ala | Thr | |
| 80 | | | | | 85 | | | | 90 | | | | | | 95 | |
| AGG | CTG | CAG | TTC | TCC | GAC | CAG | GCT | GGG | GTG | TCT | GTG | CTG | TAC | ACT | GTC | 397 |
| Arg | Leu | Gln | Phe | Ser | Asp | Gln | Ala | Gly | Val | Ser | Val | Leu | Tyr | Thr | Val | |
| | | | | 100 | | | | 105 | | | | | 110 | | | |
| ACA | CTC | TGG | GTG | GAA | TCC | TGG | GCC | AGG | AAC | CAG | ACA | GAG | AAG | TCT | CCT | 445 |
| Thr | Leu | Trp | Val | Glu | Ser | Trp | Ala | Arg | Asn | Gln | Thr | Glu | Lys | Ser | Pro | |
| | | | 115 | | | | 120 | | | | | 125 | | | | |
| GAG | GTG | ACC | CTG | CAG | CTC | TAC | AAC | TCA | GTT | AAA | TAT | GAG | CCT | CCT | CTG | 493 |
| Glu | Val | Thr | Leu | Gln | Leu | Tyr | Asn | Ser | Val | Lys | Tyr | Glu | Pro | Pro | Leu | |
| | | 130 | | | | 135 | | | | | 140 | | | | | |
| GGA | GAC | ATC | AAG | GTG | TCC | AAG | TTG | GCC | GGG | CAG | CTG | CGT | ATG | GAG | TGG | 541 |
| Gly | Asp | Ile | Lys | Val | Ser | Lys | Leu | Ala | Gly | Gln | Leu | Arg | Met | Glu | Trp | |
| | | | 145 | | | 150 | | | | | 155 | | | | | |
| GAG | ACC | CCG | GAT | AAC | CAG | GTT | GGT | GCT | GAG | GTG | CAG | TTC | CGG | CAC | CGG | 589 |
| Glu | Thr | Pro | Asp | Asn | Gln | Val | Gly | Ala | Glu | Val | Gln | Phe | Arg | His | Arg | |
| 160 | | | | | 165 | | | | | 170 | | | | | 175 | |
| ACA | CCC | AGC | AGC | CCA | TGG | AAG | TTG | GGC | GAC | TGC | GGA | CCT | CAG | GAT | GAT | 637 |
| Thr | Pro | Ser | Ser | Pro | Trp | Lys | Leu | Gly | Asp | Cys | Gly | Pro | Gln | Asp | Asp | |
| | | | | 180 | | | | 185 | | | | | 190 | | | |
| GAT | ACT | GAG | TCC | TGC | CTC | TGC | CCC | CTG | GAG | ATG | AAT | GTG | GCC | CAG | GAA | 685 |
| Asp | Thr | Glu | Ser | Cys | Leu | Cys | Pro | Leu | Glu | Met | Asn | Val | Ala | Gln | Glu | |
| | | | 195 | | | | 200 | | | | | 205 | | | | |
| TTC | CAG | CTC | CGA | CGA | CGG | CAG | CTG | GGG | AGC | CAA | GGA | AGT | TCC | TGG | AGC | 733 |
| Phe | Gln | Leu | Arg | Arg | Arg | Gln | Leu | Gly | Ser | Gln | Gly | Ser | Ser | Trp | Ser | |
| | | 210 | | | | 215 | | | | | 220 | | | | | |
| AAG | TGG | AGC | AGC | CCC | GTG | TGC | GTT | CCC | CCT | GAA | AAC | CCC | CCA | CAG | CCT | 781 |
| Lys | Trp | Ser | Ser | Pro | Val | Cys | Val | Pro | Pro | Glu | Asn | Pro | Pro | Gln | Pro | |
| | 225 | | | | | 230 | | | | | 235 | | | | | |
| CAG | GTG | AGA | TTC | TCG | GTG | GAG | CAG | CTG | GGC | CAG | GAT | GGG | AGG | AGG | CGG | 829 |
| Gln | Val | Arg | Phe | Ser | Val | Glu | Gln | Leu | Gly | Gln | Asp | Gly | Arg | Arg | Arg | |
| 240 | | | | | 245 | | | | | 250 | | | | | 255 | |
| CTG | ACC | CTG | AAA | GAG | CAG | CCA | ACC | CAG | CTG | GAG | CTT | CCA | GAA | GGC | TGT | 877 |
| Leu | Thr | Leu | Lys | Glu | Gln | Pro | Thr | Gln | Leu | Glu | Leu | Pro | Glu | Gly | Cys | |
| | | | | 260 | | | | | 265 | | | | | 270 | | |
| CAA | GGG | CTG | GCG | CCT | GGC | ACG | GAG | GTC | ACT | TAC | CGA | CTA | CAG | CTC | CAC | 925 |
| Gln | Gly | Leu | Ala | Pro | Gly | Thr | Glu | Val | Thr | Tyr | Arg | Leu | Gln | Leu | His | |
| | | | | 275 | | | | 280 | | | | | 285 | | | |
| ATG | CTG | TCC | TGC | CCG | TGT | AAG | GCC | AAG | GCC | ACC | AGG | ACC | CTG | CAC | CTG | 973 |
| Met | Leu | Ser | Cys | Pro | Cys | Lys | Ala | Lys | Ala | Thr | Arg | Thr | Leu | His | Leu | |
| | | 290 | | | | 295 | | | | | 300 | | | | | |
| GGG | AAG | ATG | CCC | TAT | CTC | TCG | GGT | GCT | GCC | TAC | AAC | GTG | GCT | GTC | ATC | 1021 |
| Gly | Lys | Met | Pro | Tyr | Leu | Ser | Gly | Ala | Ala | Tyr | Asn | Val | Ala | Val | Ile | |
| | 305 | | | | | 310 | | | | | 315 | | | | | |
| TCC | TCG | AAC | CAA | TTT | GGT | CCT | GGC | CTG | AAC | CAG | ACG | TGG | CAC | ATT | CCT | 1069 |
| Ser | Ser | Asn | Gln | Phe | Gly | Pro | Gly | Leu | Asn | Gln | Thr | Trp | His | Ile | Pro | |
| 320 | | | | | 325 | | | | | 330 | | | | | 335 | |
| GCC | GAC | ACC | CAC | ACA | GAA | CCA | GTG | GCT | CTG | AAT | ATC | AGC | GTC | GGA | ACC | 1117 |
| Ala | Asp | Thr | His | Thr | Glu | Pro | Val | Ala | Leu | Asn | Ile | Ser | Val | Gly | Thr | |
| | | | | 340 | | | | | 345 | | | | | 350 | | |
| AAC | GGG | ACC | ACC | ATG | TAT | TGG | CCA | GCC | CGG | GCT | CAG | AGC | ATG | ACG | TAT | 1165 |
| Asn | Gly | Thr | Thr | Met | Tyr | Trp | Pro | Ala | Arg | Ala | Gln | Ser | Met | Thr | Tyr | |
| | | | 355 | | | | 360 | | | | 365 | | | | | |
| TGC | ATT | GAA | TGG | CAG | CCT | GTG | GGC | CAG | GAC | GGG | GGC | CTT | GCC | ACC | TGC | 1213 |
| Cys | Ile | Glu | Trp | Gln | Pro | Val | Gly | Gln | Asp | Gly | Gly | Leu | Ala | Thr | Cys | |
| | | 370 | | | | | 375 | | | | | 380 | | | | |

| | | | | | | | | | | | | | | | | |
|---|---|---|---|---|---|---|---|---|---|---|---|---|---|---|---|---|
| AGC | CTG | ACT | GCG | CCG | CAA | GAC | CCG | GAT | CCG | GCT | GGA | ATG | GCA | ACC | TAC | 1261 |
| Ser | Leu | Thr | Ala | Pro | Gln | Asp | Pro | Asp | Pro | Ala | Gly | Met | Ala | Thr | Tyr | |
| 385 | | | | | 390 | | | | | 395 | | | | | | |
| AGC | TGG | AGT | CGA | GAG | TCT | GGG | GCA | ATG | GGG | CAG | GAA | AAG | TGT | TAC | TAC | 1309 |
| Ser | Trp | Ser | Arg | Glu | Ser | Gly | Ala | Met | Gly | Gln | Glu | Lys | Cys | Tyr | Tyr | |
| 400 | | | | | 405 | | | | | 410 | | | | | 415 | |
| ATT | ACC | ATC | TTT | GCC | TCT | GCG | CAC | CCC | GAG | AAG | CTC | ACC | TTG | TGG | TCT | 1357 |
| Ile | Thr | Ile | Phe | Ala | Ser | Ala | His | Pro | Glu | Lys | Leu | Thr | Leu | Trp | Ser | |
| | | | | 420 | | | | | 425 | | | | | 430 | | |
| ACG | GTC | CTG | TCC | ACC | TAC | CAC | TTT | GGG | GGC | AAT | GCC | TCA | GCA | GCT | GGG | 1405 |
| Thr | Val | Leu | Ser | Thr | Tyr | His | Phe | Gly | Gly | Asn | Ala | Ser | Ala | Ala | Gly | |
| | | | 435 | | | | | 440 | | | | | 445 | | | |
| ACA | CCG | CAC | CAC | GTC | TCG | GTG | AAG | AAT | CAT | AGC | TTG | GAC | TCT | GTG | TCT | 1453 |
| Thr | Pro | His | His | Val | Ser | Val | Lys | Asn | His | Ser | Leu | Asp | Ser | Val | Ser | |
| | | 450 | | | | | 455 | | | | | 460 | | | | |
| GTG | GAC | TGG | GCA | CCA | TCC | CTG | CTG | AGC | ACC | TGT | CCC | GGC | GTC | CTA | AAG | 1501 |
| Val | Asp | Trp | Ala | Pro | Ser | Leu | Leu | Ser | Thr | Cys | Pro | Gly | Val | Leu | Lys | |
| | 465 | | | | | 470 | | | | | 475 | | | | | |
| GAG | TAT | GTT | GTC | CGC | TGC | CGA | GAT | GAA | GAC | AGC | AAA | CAG | GTG | TCA | GAG | 1549 |
| Glu | Tyr | Val | Val | Arg | Cys | Arg | Asp | Glu | Asp | Ser | Lys | Gln | Val | Ser | Glu | |
| 480 | | | | | 485 | | | | | 490 | | | | | 495 | |
| CAT | CCC | GTG | CAG | CCC | ACA | GAG | ACC | CAA | GTT | ACC | CTC | AGT | GGC | CTG | CGG | 1597 |
| His | Pro | Val | Gln | Pro | Thr | Glu | Thr | Gln | Val | Thr | Leu | Ser | Gly | Leu | Arg | |
| | | | | 500 | | | | | 505 | | | | | 510 | | |
| GCT | GGT | GTA | GCC | TAC | ACG | GTG | CAG | GTG | CGA | GCA | GAC | ACA | GCG | TGG | CTG | 1645 |
| Ala | Gly | Val | Ala | Tyr | Thr | Val | Gln | Val | Arg | Ala | Asp | Thr | Ala | Trp | Leu | |
| | | | 515 | | | | | 520 | | | | | 525 | | | |
| AGG | GGT | GTC | TGG | AGC | CAG | CCC | CAG | CGC | TTC | AGC | ATC | GAA | GTG | CAG | GTT | 1693 |
| Arg | Gly | Val | Trp | Ser | Gln | Pro | Gln | Arg | Phe | Ser | Ile | Glu | Val | Gln | Val | |
| | | 530 | | | | | 535 | | | | | 540 | | | | |
| TCT | GAT | TGG | CTC | ATC | TTC | TTC | GCC | TCC | CTG | GGG | AGC | TTC | CTG | AGC | ATC | 1741 |
| Ser | Asp | Trp | Leu | Ile | Phe | Phe | Ala | Ser | Leu | Gly | Ser | Phe | Leu | Ser | Ile | |
| | 545 | | | | | 550 | | | | | 555 | | | | | |
| CTT | CTC | GTG | GGC | GTC | CTT | GGC | TAC | CTT | GGC | CTG | AAC | AGG | GCC | GCA | CGG | 1789 |
| Leu | Leu | Val | Gly | Val | Leu | Gly | Tyr | Leu | Gly | Leu | Asn | Arg | Ala | Ala | Arg | |
| 560 | | | | | 565 | | | | | 570 | | | | | 575 | |
| CAC | CTG | TGC | CCG | CCG | CTG | CCC | ACA | CCC | TGT | GCC | AGC | TCC | GCC | ATT | GAG | 1837 |
| His | Leu | Cys | Pro | Pro | Leu | Pro | Thr | Pro | Cys | Ala | Ser | Ser | Ala | Ile | Glu | |
| | | | | 580 | | | | | 585 | | | | | 590 | | |
| TTC | CCT | GGA | GGG | AAG | GAG | ACT | TGG | CAG | TGG | ATC | AAC | CCA | GTG | GAC | TTC | 1885 |
| Phe | Pro | Gly | Gly | Lys | Glu | Thr | Trp | Gln | Trp | Ile | Asn | Pro | Val | Asp | Phe | |
| | | | 595 | | | | | 600 | | | | | 605 | | | |
| CAG | GAA | GAG | GCA | TCC | CTG | CAG | GAG | GCC | CTG | GTG | GTA | GAG | ATG | TCC | TGG | 1933 |
| Gln | Glu | Glu | Ala | Ser | Leu | Gln | Glu | Ala | Leu | Val | Val | Glu | Met | Ser | Trp | |
| | | 610 | | | | | 615 | | | | | 620 | | | | |
| GAC | AAA | GGC | GAG | AGG | ACT | GAG | CCT | CTC | GAG | AAG | ACA | GAG | CTA | CCT | GAG | 1981 |
| Asp | Lys | Gly | Glu | Arg | Thr | Glu | Pro | Leu | Glu | Lys | Thr | Glu | Leu | Pro | Glu | |
| | 625 | | | | | 630 | | | | | 635 | | | | | |
| GGT | GCC | CCT | GAG | CTG | GCC | CTG | GAT | ACA | GAG | TTG | TCC | TTG | GAG | GAT | GGA | 2029 |
| Gly | Ala | Pro | Glu | Leu | Ala | Leu | Asp | Thr | Glu | Leu | Ser | Leu | Glu | Asp | Gly | |
| 640 | | | | | 645 | | | | | 650 | | | | | 655 | |
| GAC | AGG | TGC | AAG | GCC | AAG | ATG | TGATCGTTGA | | GGCTCAGAGA | | GGGTGAGTGA | | | | | 2080 |
| Asp | Arg | Cys | Lys | Ala | Lys | Met | | | | | | | | | | |
| | | | | 660 | | | | | | | | | | | | |

CTCGCCCGAG GCTACGTAGC CTTT 2104

( 2 ) INFORMATION FOR SEQ ID NO:4:

( i ) SEQUENCE CHARACTERISTICS:
( A ) LENGTH: 662 amino acids (B) TYPE: amino acid
(D) TOPOLOGY: linear (ii) MOLECULE TYPE: protein (ix) FEATURE:
    (A) NAME/KEY: Region
    (B) LOCATION: 1..20
    (D) OTHER INFORMATION: /note= "N-terminal signal peptide (1..20 or 23 or 24)"

(ix) FEATURE:
    (A) NAME/KEY: Region
    (B) LOCATION: 541..570
    (D) OTHER INFORMATION: /note= "transmembrane region"

(ix) FEATURE:
    (A) NAME/KEY: Region
    (B) LOCATION: 571..662
    (D) OTHER INFORMATION: /note= "cytoplasmic tail region"

(ix) FEATURE:
    (A) NAME/KEY: Region
    (B) LOCATION: 52..64
    (D) OTHER INFORMATION: /note= "sequence motif of cytokine receptor superfamily Cys52..Cys62SW"

(ix) FEATURE:
    (A) NAME/KEY: Region
    (B) LOCATION: 222..226
    (D) OTHER INFORMATION: /note= "cytokine receptor superfamily motif (W222SKWS)"

(ix) FEATURE:
    (A) NAME/KEY: Region
    (B) LOCATION: 121..123
    (D) OTHER INFORMATION: /note= "N-linked glycosylation site"

(ix) FEATURE:
    (A) NAME/KEY: Region
    (B) LOCATION: 329..331
    (D) OTHER INFORMATION: /note= "N-linked glycosylation site"

(ix) FEATURE:
    (A) NAME/KEY: Region
    (B) LOCATION: 346..348
    (D) OTHER INFORMATION: /note= "N-linked glycosylation site"

(ix) FEATURE:
    (A) NAME/KEY: Region
    (B) LOCATION: 352..354
    (D) OTHER INFORMATION: /note= "N-linked glycosylation site"

(ix) FEATURE:
    (A) NAME/KEY: Region
    (B) LOCATION: 442..444
    (D) OTHER INFORMATION: /note= "N-linked glycosylation site"

(ix) FEATURE:
    (A) NAME/KEY: Region
    (B) LOCATION: 456..458
    (D) OTHER INFORMATION: /note= "N-linked glycosylation site"

(ix) FEATURE:
    (A) NAME/KEY: Region
    (B) LOCATION: 24..540
    (D) OTHER INFORMATION: /note= "Extracellular region"

(xi) SEQUENCE DESCRIPTION: SEQ ID NO:4:

| Met | Glu | Pro | Leu | Val | Thr | Trp | Val | Val | Pro | Leu | Leu | Phe | Leu | Phe |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Leu | Ser | Arg | Gln | Gly | Ala | Ala | Cys | Arg | Thr | Ser | Glu | Cys | Cys | Phe | Gln |

-continued

|  |  |  | 20 |  |  |  | 25 |  |  |  | 30 |  |  |
|---|---|---|---|---|---|---|---|---|---|---|---|---|---|

Asp Pro Pro Tyr Pro Asp Ala Asp Ser Gly Ser Ala Ser Gly Pro Arg
        35              40              45
Asp Leu Arg Cys Tyr Arg Ile Ser Ser Asp Arg Tyr Glu Cys Ser Trp
    50              55              60
Gln Tyr Glu Gly Pro Thr Ala Gly Val Ser His Phe Leu Arg Cys Cys
65              70              75              80
Leu Ser Ser Gly Arg Cys Cys Tyr Phe Ala Ala Gly Ser Ala Thr Arg
            85              90              95
Leu Gln Phe Ser Asp Gln Ala Gly Val Ser Val Leu Tyr Thr Val Thr
            100             105             110
Leu Trp Val Glu Ser Trp Ala Arg Asn Gln Thr Glu Lys Ser Pro Glu
        115             120             125
Val Thr Leu Gln Leu Tyr Asn Ser Val Lys Tyr Glu Pro Pro Leu Gly
        130             135             140
Asp Ile Lys Val Ser Lys Leu Ala Gly Gln Leu Arg Met Glu Trp Glu
145             150             155             160
Thr Pro Asp Asn Gln Val Gly Ala Glu Val Gln Phe Arg His Arg Thr
                165             170             175
Pro Ser Ser Pro Trp Lys Leu Gly Asp Cys Gly Pro Gln Asp Asp
            180             185             190
Thr Glu Ser Cys Leu Cys Pro Leu Glu Met Asn Val Ala Gln Glu Phe
        195             200             205
Gln Leu Arg Arg Arg Gln Leu Gly Ser Gln Gly Ser Ser Trp Ser Lys
        210             215             220
Trp Ser Ser Pro Val Cys Val Pro Pro Glu Asn Pro Pro Gln Pro Gln
225             230             235             240
Val Arg Phe Ser Val Glu Gln Leu Gly Gln Asp Gly Arg Arg Arg Leu
            245             250             255
Thr Leu Lys Glu Gln Pro Thr Gln Leu Glu Leu Pro Glu Gly Cys Gln
            260             265             270
Gly Leu Ala Pro Gly Thr Glu Val Thr Tyr Arg Leu Gln Leu His Met
        275             280             285
Leu Ser Cys Pro Cys Lys Ala Lys Ala Thr Arg Thr Leu His Leu Gly
    290             295             300
Lys Met Pro Tyr Leu Ser Gly Ala Ala Tyr Asn Val Ala Val Ile Ser
305             310             315             320
Ser Asn Gln Phe Gly Pro Gly Leu Asn Gln Thr Trp His Ile Pro Ala
            325             330             335
Asp Thr His Thr Glu Pro Val Ala Leu Asn Ile Ser Val Gly Thr Asn
        340             345             350
Gly Thr Thr Met Tyr Trp Pro Ala Arg Ala Gln Ser Met Thr Tyr Cys
        355             360             365
Ile Glu Trp Gln Pro Val Gly Gln Asp Gly Gly Leu Ala Thr Cys Ser
    370             375             380
Leu Thr Ala Pro Gln Asp Pro Asp Pro Ala Gly Met Ala Thr Tyr Ser
385             390             395             400
Trp Ser Arg Glu Ser Gly Ala Met Gly Gln Glu Lys Cys Tyr Tyr Ile
            405             410             415
Thr Ile Phe Ala Ser Ala His Pro Glu Lys Leu Thr Leu Trp Ser Thr
        420             425             430
Val Leu Ser Thr Tyr His Phe Gly Gly Asn Ala Ser Ala Ala Gly Thr
        435             440             445

| | | | | | | | | | | | | | | |
|---|---|---|---|---|---|---|---|---|---|---|---|---|---|---|
| Pro | His 450 | His | Val | Ser | Val | Lys 455 | Asn | His | Ser | Leu | Asp 460 | Ser | Val | Ser | Val |
| Asp 465 | Trp | Ala | Pro | Ser | Leu 470 | Leu | Ser | Thr | Cys | Pro 475 | Gly | Val | Leu | Lys | Glu 480 |
| Tyr | Val | Val | Arg | Cys 485 | Arg | Asp | Glu | Asp | Ser 490 | Lys | Gln | Val | Ser | Glu 495 | His |
| Pro | Val | Gln | Pro 500 | Thr | Glu | Thr | Gln | Val 505 | Thr | Leu | Ser | Gly | Leu 510 | Arg | Ala |
| Gly | Val | Ala 515 | Tyr | Thr | Val | Gln | Val 520 | Arg | Ala | Asp | Thr | Ala 525 | Trp | Leu | Arg |
| Gly | Val 530 | Trp | Ser | Gln | Pro | Gln 535 | Arg | Phe | Ser | Ile | Glu 540 | Val | Gln | Val | Ser |
| Asp 545 | Trp | Leu | Ile | Phe | Phe 550 | Ala | Ser | Leu | Gly | Ser 555 | Phe | Leu | Ser | Ile | Leu 560 |
| Leu | Val | Gly | Val | Leu 565 | Gly | Tyr | Leu | Gly | Leu 570 | Asn | Arg | Ala | Ala | Arg 575 | His |
| Leu | Cys | Pro | Pro 580 | Leu | Pro | Thr | Pro | Cys 585 | Ala | Ser | Ser | Ala | Ile 590 | Glu | Phe |
| Pro | Gly | Gly 595 | Lys | Glu | Thr | Trp | Gln 600 | Trp | Ile | Asn | Pro | Val 605 | Asp | Phe | Gln |
| Glu | Glu 610 | Ala | Ser | Leu | Gln | Glu 615 | Ala | Leu | Val | Val | Glu 620 | Met | Ser | Trp | Asp |
| Lys 625 | Gly | Glu | Arg | Thr | Glu 630 | Pro | Leu | Glu | Lys | Thr 635 | Glu | Leu | Pro | Glu | Gly 640 |
| Ala | Pro | Glu | Leu | Ala 645 | Leu | Asp | Thr | Glu | Leu 650 | Ser | Leu | Glu | Asp | Gly 655 | Asp |
| Arg | Cys | Lys | Ala 660 | Lys | Met | | | | | | | | | | |